US009440984B2

(12) United States Patent
Haltiwanger et al.

(10) Patent No.: US 9,440,984 B2
(45) Date of Patent: Sep. 13, 2016

(54) PYRROLOTRIAZINES AS ALK INHIBITORS

(71) Applicant: Cephalon, Inc., Frazer, PA (US)

(72) Inventors: Ralph C. Haltiwanger, West Chester, PA (US); Eugen F. Mesaros, Wallingford, PA (US); Gregory R. Ott, Media, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 14/944,668

(22) Filed: Nov. 18, 2015

(65) Prior Publication Data

US 2016/0068535 A1 Mar. 10, 2016

Related U.S. Application Data

(63) Continuation of application No. PCT/US2014/039755, filed on May 28, 2014.

(60) Provisional application No. 61/828,451, filed on May 29, 2013.

(51) Int. Cl.
*C07D 487/04* (2006.01)
*A61K 31/53* (2006.01)

(52) U.S. Cl.
CPC ............. *C07D 487/04* (2013.01); *A61K 31/53* (2013.01)

(58) Field of Classification Search
None
See application file for complete search history.

(56) References Cited

U.S. PATENT DOCUMENTS 7,973,061 B2 7/2011 Leahy et al.
8,471,005 B2 6/2013 Breslin et al.

FOREIGN PATENT DOCUMENTS

WO WO 2005/009389 A2 2/2005
WO WO 2005/016894 A1 2/2005
WO WO 2005/080393 A1 9/2005

OTHER PUBLICATIONS

Database CAPLUS in STN, Acc. No. 2010:785034, Breslin et al., WO 2010071885 A1 (Jun. 24, 2010) (abstract).*
Armitage et al., *Cancer: Principle and Practice of Oncology*, 6th ed. (2001), pp. 2256-2316.
Bai et al., "Nucleophosmin-anaplastic lymphoma kinase associated with anaplastic large-cell lymphoma activates the phosphatidylinositol 3-kinase/Akt antiapoptotic signaling pathway," *Blood* (2000) 96, pp. 4319-4327.
Bai et al., "Nucleophosmin-Anaplastic Lymphoma Kinase of Large-Cell Anaplastic Lymphoma is a Constitutively Active Tyrosine Kinase that Utilizes Phospholipase C-γ to Mediate its Mitogenicity," *Molecular and Cellular Biology* (1998) 18, pp. 6951-6961.

Berge et al., "Pharmaceutical Salts," *J. Pharm. Sci.* (1977) 66, pp. 1-19.
Cheng et al., "CEP-28122, a Highly Potent and Selective Orally Active Inhibitor of Anaplastic Lymphoma Kinase with Antitumor Activity in Experimental Models of Human Cancers," *Mol. Cancer Ther.* (2011) 11, pp. 670-679.
Duyster et al., "Translocations Involving Anaplastic Lymphoma Kinase (ALK)," *Oncogene* (2001) 20, pp. 5623-5637.
Ergin et al., "Inhibition of tyrosine kinase activity induces caspase-dependent apoptosis in anaplastic large cell lymphoma with NPM-ALK (p80) fusion protein," *Experimental Hematology* (2001) 29, pp. 1082-1090.
Falini et al., "Lymphomas Expressing ALK Fusion Protein(s) Other Than NPM-ALK," *Blood* (1999) 94, pp. 3509-3515.
Ferreri et al., "Anaplastic Large Cell Lymphoma, ALK-positive," *Critical Rev. Oncology Hematology* (2012) 83, pp. 293-302.
Kuefer et al., "Retrovirus-Mediated Gene Transfer of NPM-ALK Causes Lymphoid Malignaucy in Mice," *Blood* (1997) 90, pp. 2901-2910.
Kutok et al., "Molecular Biology of Anaplastic Lymphoma Kinase-Positive Anaplastic Large-Cell Lymphoma," *J. Clin. Oncology* (2002) 20, pp. 3691-3702.
Lawrence et al., "TPM3-ALK and TPM4-ALK Oncogenes in Inflammatory Myofibroblastic Tumors," *Am. J. Pathology* (2000) 157, pp. 377-384.
Mentlein et al., "Pleiotrophin, an angiogenic and mitogenic growth factor, is expressed in human gliomas," *J. Neurochem.* (2002) 83, pp. 747-753.
Mesaros et al., "Strategies to Mitigate the Bioactivation of 2-Anilino-7-aryl-Pyrrolo[2,1-f][1,2,4]triazines: Identification of Orally Bioavailable, Efficacious ALK Inhibitors," *J. Med. Chem.* (2012) 55, pp. 115-125.

(Continued)

*Primary Examiner* — Brian J Davis

(57) ABSTRACT

This application provides compounds of the general formula (I)

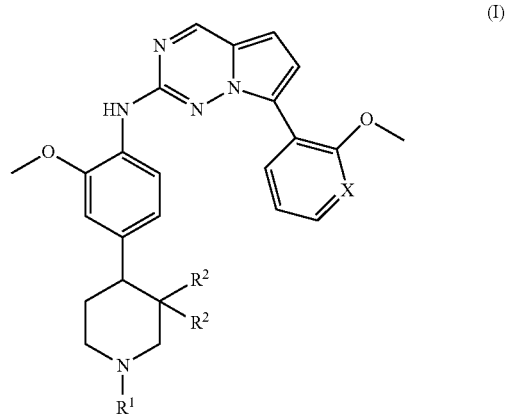

and/or a salt thereof, where X, $R^1$ and $R^2$ are as defined herein. Compositions and therapeutic uses are also described.

20 Claims, 3 Drawing Sheets

(56) References Cited

OTHER PUBLICATIONS

Morris et al., "ALK+ CD30+ Lymphomas: A Distinct Molecular Genetic Subtype of Non-Hodgkin's Lymphoma," *Br. J. Haematology* (2001) 113, pp. 275-295.

Mudianta et al., "Structure and Absolute Configuration of 3-alkylpiperidine Alkaloids from an Indonesian Sponge of the Genus *Halichondria*," *Tetrahedron* (2010) 66, pp. 2752-2760.

Ott et al., "2,7-Disubstituted-pyrrolo[2,1-f][1,2,4]triazines: New Variant of an Old Template and Application to the Discovery of Anaplastic Lymphoma Kinase (ALK) Inhibitors with in Vivo Antitumor Activity," *J. Med. Chem.* (2011) 54, pp. 6328-6341.

Powers et al., "Pleiotrophin Signaling through Anaplastic Lymphoma Kinase is Rate-limiting for Glioblastoma Growth," *J. Biological Chem.* (2002) 277, pp. 14153-14158.

Roskoski, "Anaplastic Lymphoma Kinase (ALK): Structure, Oncogenic Activation, and Pharmacological Inhibition," *Pharmacological Res.* (2013) 68, pp. 68-94.

Slupianek et al., "Role of Phosphatidylinositol 3-Kinase-Akt Pathway in Nucleophosmin/Anaplastic Lymphoma Kinase-mediated Lymphomagenesis," *Cancer Res.* (2001) 61, pp. 2194-2199.

Soda et al., "Identification of the transforming EML4-ALK fusion gene in non-small-cell lung cancer," *Nature* (2007) 448, pp. 561-566.

Stoica et al., "Identification of Anaplastic Lymphoma Kinase as a Receptor for the Growth Factor Pleiotrophin," *J. Biological Chem.* (2001) 276, pp. 16772-16779.

Turturro et al., "Model of Inhibition of the NPM-ALK Kinase Activity by Herbimycin A," *Clin. Cancer Res.* (2002) 8, pp. 240-245.

Weinberg et al., "2,7-Pyrrolo[2,1-f][1,2,4]triazines as JAK2 Inhibitors: Modification of Target Structure to Minimize Reactive Metabolite Formation," *Bioorg. & Med. Chem. Letts.* (2011) 21, pp. 7325-7330.

\* cited by examiner

PYRROLOTRIAZINES AS ALK INHIBITORS

CROSS REFERENCE TO RELATED APPLICATIONS

This application is a continuation of International Application No. PCT/US2014/039755, filed May 28, 2014, which claims the benefit of U.S. Provisional Application No. 61/828,451, filed May 29, 2013, the disclosures of which are incorporated herein by reference in their entireties.

BACKGROUND

Anaplastic Lymphoma Kinase (ALK) is a cell membrane-spanning receptor tyrosine kinase, which belongs to the insulin receptor subfamily. The most abundant expression of ALK occurs in the neonatal brain, suggesting a possible role for ALK in brain development (Duyster, J. et al., *Oncogene*, 2001, 20, 5623-5637).

ALK is also implicated in the progression of certain tumors. For example, approximately sixty percent of anaplastic large cell lymphomas (ALCL) are associated with a chromosome mutation that generates a fusion protein consisting of nucleophosmin (NPM) and the intracellular domain of ALK. (Armitage, J. O. et al., *Cancer: Principle and Practice of Oncology*, 6$^{th}$ edition, 2001, 2256-2316; Kutok J. L. & Aster J. C., *J. Clin. Oncol.*, 2002, 20, 3691-3702). This mutant protein, NPM-ALK, possesses a constitutively active tyrosine kinase domain that is responsible for its oncogenic property through activation of downstream effectors. (Falini, B. et al., *Blood*, 1999, 94, 3509-3515; Morris, S. W. et al., *Brit. J. Haematol.*, 2001, 113, 275-295; Duyster et al.; Kutok & Aster). In addition, the transforming EML4-ALK fusion gene has been identified in non-small-cell lung cancer (NSCLC) patients (Soda, M., et al., *Nature*, 2007, 448, 561-566) and represents another in a list of ALK fusion proteins that are promising targets for ALK inhibitor therapy. Experimental data have demonstrated that the aberrant expression of constitutively active ALK is directly implicated in the pathogenesis of ALCL and that inhibition of ALK can markedly impair the growth of ALK+lymphoma cells (Kuefer, Mu et al. *Blood*, 1997, 90, 2901-2910; Bai, R. Y. et al., *Mol. Cell Biol.*, 1998, 18, 6951-6961; Bai, R. Y. et al., *Blood*, 2000, 96, 4319-4327; Ergin, M. et al., *Exp. Hematol.*, 2001, 29, 1082-1090; Slupianek, A. et al., *Cancer Res.*, 2001, 61, 2194-2199; Turturro, F. et al., *Clin. Cancer Res.*, 2002, 8, 240-245). The constitutively activated chimeric ALK has also been demonstrated in about 60% of inflammatory myofibroblastic tumors (IMTs), a slow-growing sarcoma that mainly affects children and young adults. (Lawrence, B. et al., *Am. J. Pathol.*, 2000, 157, 377-384; Duyster et al.).

In addition, ALK and its putative ligand, pleiotrophin, are overexpressed in human glioblastomas (Stoica, G. et al., *J. Biol. Chem.*, 2001, 276, 16772-16779). In mouse studies, depletion of ALK reduced glioblastoma tumor growth and prolonged animal survival (Powers, C. et al., *J. Biol. Chem.*, 2002, 277, 14153-14158; Mentlein, R. et al, *J. Neurochem.*, 2002, 83, 747-753).

It is thought that ALK inhibitors would permit durable cures when combined with current chemotherapy for ALCL, IMT, proliferative disorders, glioblastoma and possible other solid tumors, or, as a single therapeutic agent, could be used in a maintenance role to prevent cancer recurrence in those patients. Various ALK inhibitors have been reported, such as indazoloisoquinolines (WO 2005/009389), thiazole amides and oxazole amides (WO 2005/097765), pyrrolopyrimidines (WO 2005080393), and pyrimidinediamines (WO 2005/016894).

In summary, there is clear genetic and biological evidence that links aberrant ALK activation with the onset and progression of certain types of cancer in humans. Considerable evidence indicates that ALK-positive tumor cells require these oncogenes to proliferate and survive, while inhibition of ALK signaling leads to tumor cell growth arrest or apoptosis, resulting in objective cytoreductive effects. ALK is minimally expressed in most normal tissues in the healthy adult and are activated and/or dysregulated in specific cancers during oncogenesis and/or during early stages of malignant progression. Consequently, the on-target effects of treatment with an ALK inhibitor against normal cells should be minimal, creating a favorable therapeutic index.

SUMMARY

This application provides compounds of the general formula (I)

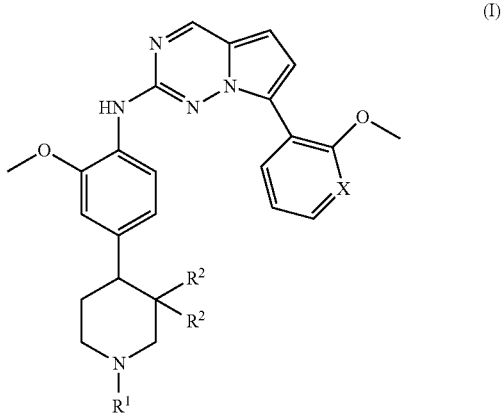

and/or a salt thereof.

Compounds of formula (I) have ALK inhibitory activity, and may be used to treat ALK mediated disorders or conditions.

This application further provides pharmaceutical compositions comprising at least one compound of formula (I) or a salt thereof together with at least one pharmaceutically acceptable excipient.

DETAILED DESCRIPTION

I. Definitions

Figure 1:
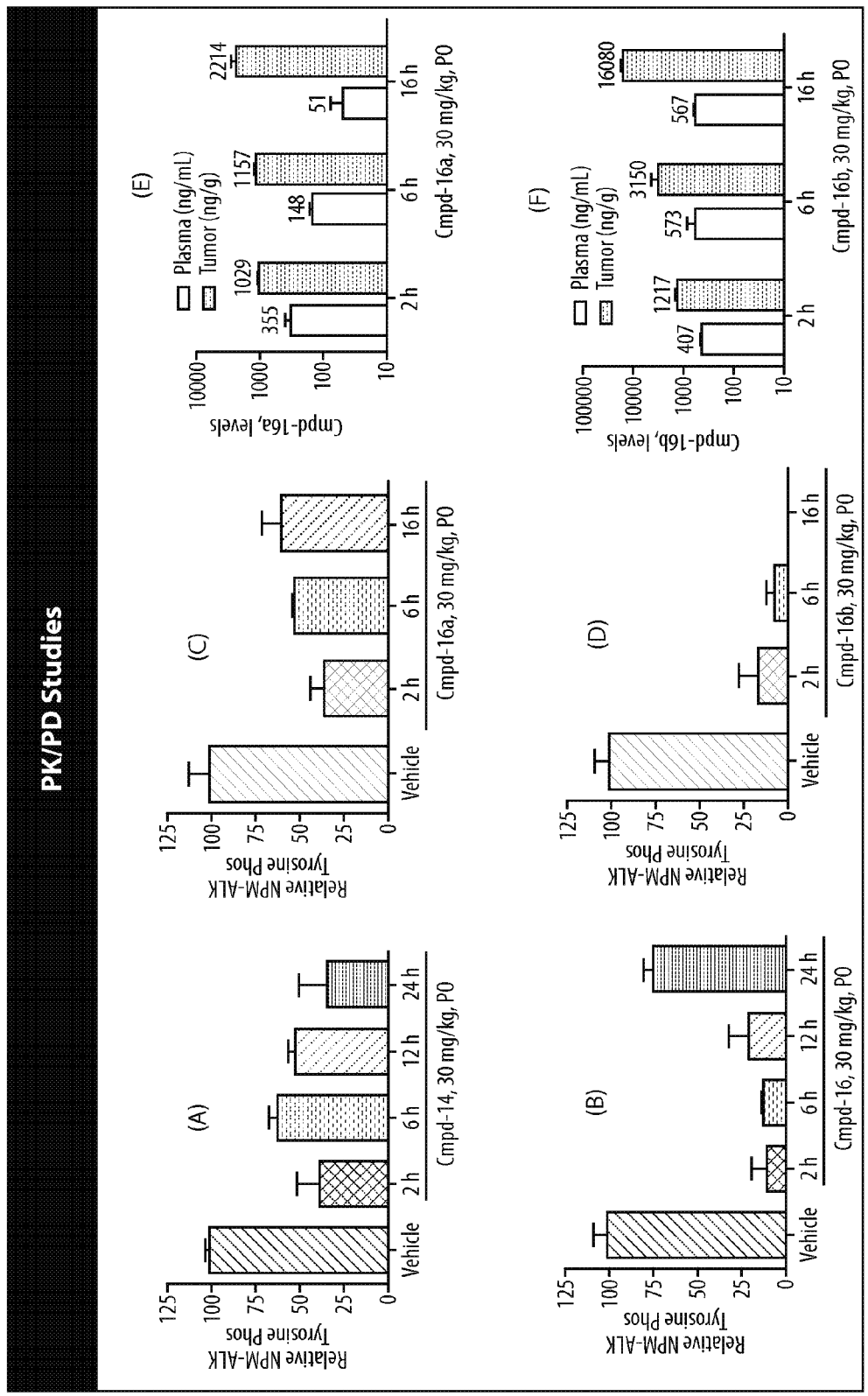
FIG. 1 depicts pharmacokinetic/pharmacodynamic data from studies in SCID mice bearing Sup-M2 human anaplastic large cell lymphoma (ALCL) xenografts dosed orally with select compounds described herein.

As used herein, the following terms have the meanings ascribed to them unless specified otherwise.

The compounds and intermediates described herein may be named according to either the IUPAC (International Union for Pure and Applied Chemistry) or CAS (Chemical Abstracts Service) nomenclature systems.

The term "$C_{x-y}$" indicates the number of carbon atoms in a group. For example, a "$C_{1-6}$-alkyl" is an alkyl group having from one (1) to six (6) carbon atoms. In some instances, x=0, i.e., "$C_{0-y}$". The term "$C_{0-y}$" indicates that the group may be absent or present, and if present, defines the number of carbon atoms in the group. For example, "$C_{0-6}$-alkyl" indicates that an alkyl group may be absent (x=0) or present (x=1-6), and if present contains from one (1) to six (6) carbon atoms. For example, "—$C_{0-6}$-alkyl-C(=O)—$C_{0-6}$-alkyl-" includes —C(=O)—, —$C_{1-6}$-alkyl-C(=O)—, and —$C_{1-6}$-alkyl-C(=O)—$C_{1-6}$-alkyl-. Examples of —$C_{0-6}$-alkyl-C(=O)—$C_{0-6}$-alkyl-include, but are not limited to, —C(=O)—, —$CH_2CH_2$—C(=O)—, and —CH($CH_3$)$CH_2CH_2$—C(=O)—$CH_2$—.

As used by themselves or in conjunction with another term or terms, "alkyl" or "alkyl group" refers to a monoradical of a branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, isopropyl, tert-butyl, isobutyl, etc. Alkyl groups typically contain 1-10 carbon atoms, such as 1-6 carbon atoms, and can be substituted or unsubstituted.

As used by itself or in conjunction with another term or terms, "alkyloxy" refers to straight or branched hydrocarbon groups containing the requisite number of carbon atoms (an alkyl group) as described above, bonded to an oxygen atom. As used herein, alkyloxy groups may be optionally substituted with between one to four substituents. Representative examples of alkyloxy groups include, but are not limited to, e.g. methoxy, ethoxy, tert-butoxy, etc.

"Halogen" includes fluorine, chlorine, bromine and iodine atoms.

"Pharmaceutical composition" refers to a composition having a safety/efficacy profile suitable for administration to a human.

"Pharmaceutically acceptable excipient" refers to physiologically tolerable materials, which do not typically produce an allergic or other untoward reaction, such as gastric upset, dizziness and the like, when administered to a human.

"Pharmaceutically acceptable salt" refers to a salt having a safety/efficacy profile suitable for administration to a human.

"Subject" refers to a member of the class Mammalia. Examples of mammals include, without limitation, humans, primates, chimpanzees, rodents, mice, rats, rabbits, horses, livestock, dogs, cats, sheep, and cows.

"Therapeutically effective amount" refers to an amount of a compound sufficient to improve or inhibit worsening of symptoms associated with a disorder or condition being treated in a particular subject or subject population. It should be appreciated that determination of proper dosage forms, dosage amounts, and routes of administration is within the level of ordinary skill in the pharmaceutical and medical arts. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

"Treatment" refers to the acute or prophylactic diminishment or alleviation of at least one symptom or characteristic associated or caused by a disorder being treated. For example, treatment can include diminishment of a symptom of a disorder or complete eradication of a disorder.

"Administering" refers to the method of contacting a compound with a subject. Modes of "administering" include, but are not limited to, methods that involve contacting the compound intravenously, intraperitoneally, intranasally, transdermally, topically, via implantation, subcutaneously, parentally, intramuscularly, orally, systemically, and via adsorption.

For the purposes of this application, the term "and/or" should be understood as designating alternatives (this "or" that) as well as combinations (this "and" that).

II. Compounds

This application provides compounds of the general formula (I)

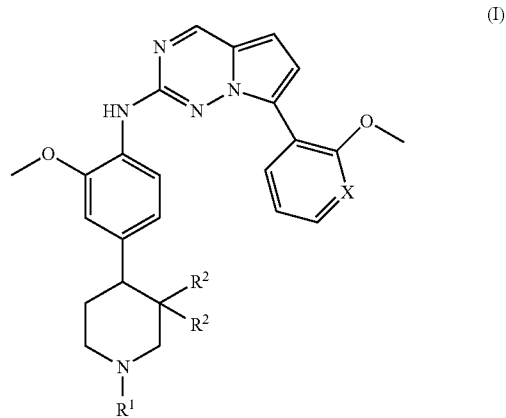

and/or a salt thereof, wherein:

X is CH or N;

$R^1$ is chosen from H or $C_1$-$C_6$alkyl substituted with at least one $R^3$;

at least one $R^2$ is halogen and the other $R^2$ is chosen from hydrogen or halogen;

each $R^3$ is independently chosen from hydroxyl, $C_1$-$C_6$alkoxy, —(CO)N($R^4$)$_2$, and —O(CO)$R^4$; and each $R^4$ is independently chosen from hydrogen, $C_1$-$C_6$alkyl, and phenyl substituted with at least one halogen.

In some embodiments, at least one $R^2$ is a halogen and the other $R^2$ is hydrogen. In other embodiments, both $R^2$ groups are halogen. In further embodiments, at least one $R^2$ is fluorine. In still further embodiments both $R^2$ groups are fluorine.

In additional embodiments X is CH. In still other embodiments X is N. In yet further embodiments X is CH and at least one $R^2$ is a halogen and the other $R^2$ is hydrogen and/or X is CH and both $R^2$ groups are halogen. In still other embodiments X is N and at least one $R^2$ is a halogen and the other $R^2$ is hydrogen and/or X is N and both $R^2$ groups are halogen.

In some embodiments, $R^1$ is H. In other embodiments, $R^1$ is H, X is N and at least one $R^2$ is a halogen and the other $R^2$ is hydrogen and/or $R^1$ is H, X is N and both $R^2$ groups are halogen. In some other embodiments, $R^1$ is H, X is CH and at least one R² is a halogen and the other R² is hydrogen and/or R¹ is H, X is CH and both R² groups are halogen.

In other embodiments, R¹ is $C_1$-$C_6$alkyl optionally substituted with at least one R³. In some embodiments, R³ is hydroxyl. In other embodiments, R³ is $C_1$-$C_6$alkoxy. In yet other embodiments, R³ is —(CO)N(R⁴)₂. In still further embodiments, R³ is —O(CO)R⁴.

In further embodiments, R⁴ is hydrogen. In yet further embodiments, R⁴ is $C_1$-$C_6$alkyl. In additional embodiments, R⁴ is phenyl substituted with at least one halogen. In still other embodiments, R⁴ is phenyl substituted with at least one bromine.

It should be understood that all stereochemical configurations, including individual enantiomers, diastereoisomers and/or mixtures of stereoisomers (in any and all ratios), are included in the description of formula (I). In particular, this application provides compounds of formula (I) that may be isolated as racemic diastereomers (namely the 3,4-Cis or 3,4-Trans stereoisomers) as well as the single enantiomers of such compounds, and any and all mixtures thereof. For example, this application provides compounds of formula (I), or a salt thereof, where R² is not hydrogen having any one of the following configurations:

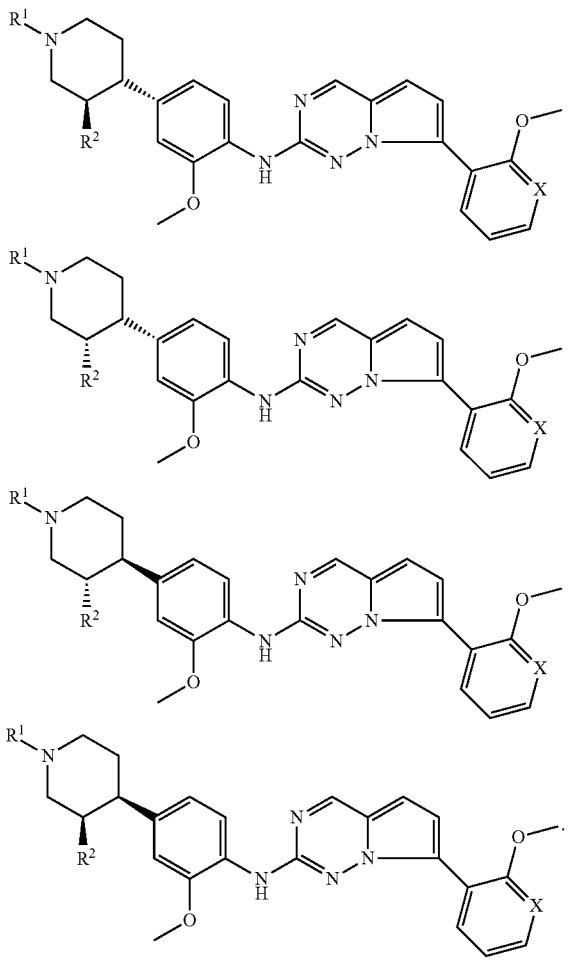

In some embodiments, these compounds are isolated as single enantiomers.

In still other additional embodiments, this application provides compounds that are chosen from:

(±)-3,4-cis-1-(2-Methoxy-ethyl)-4-{3-methoxy-4-[7-(2-methoxy-phenyl)-pyrrolo[2,1-f][1,2,4]triazin-2-ylamino]-phenyl}-piperidin-3-ol;

(±)-3,4-cis-1-(2-Hydroxy-ethyl)-4-{3-methoxy-4-[7-(2-methoxy-pyridin-3-yl)-pyrrolo[2,1-f][1,2,4]triazin-2-ylamino]-phenyl}-piperidin-3-ol;

(±)-2-(3,4-trans-3-Fluoro-4-{3-methoxy-4-[7-(2-methoxy-phenyl)-pyrrolo[2,1-f][1,2,4]triazin-2-ylamino]-phenyl}-piperidin-1-yl)-ethanol;

(±)-3,4-cis-4-{3-Methoxy-4-[7-(2-methoxy-pyridin-3-yl)-pyrrolo[2,1-f][1,2,4]triazin-2-ylamino]-phenyl}-piperidin-3-ol;

(±)-[4-(3,4-trans-3-Fluoro-piperidin-4-yl)-2-methoxy-phenyl]-[7-(2-methoxy-phenyl)-pyrrolo[2,1-f][1,2,4]triazin-2-yl]-amine;

(±)-2-(3,4-trans-3-fluoro-4-{3-methoxy-4-[7-(2-methoxy-pyridin-3-yl)-pyrrolo[2,1-f][1,2,4]triazin-2-ylamino]-phenyl}-piperidin-1-yl)-ethanol;

(±)-2-(3,3-Difluoro-4-{3-methoxy-4-[7-(2-methoxy-phenyl)-pyrrolo[2,1-f][1,2,4]triazin-2-ylamino]-phenyl}-piperidin-1-yl)-ethanol;

(±)-1-(3,4-trans-3-Fluoro-4-{3-methoxy-4-[7-(2-methoxy-pyridin-3-yl)-pyrrolo[2,1-f][1,2,4]triazin-2-ylamino]-phenyl}-piperidin-1-yl)-2-methyl-propan-2-ol;

(±)-2-(3,3-Difluoro-4-{3-methoxy-4-[7-(2-methoxy-pyridin-3-yl)-pyrrolo[2,1-f][1,2,4]triazin-2-ylamino]-phenyl}-piperidin-1-yl)-ethanol;

(±)-[4-(3,3-Difluoro-piperidin-4-yl)-2-methoxy-phenyl]-[7-(2-methoxy-pyridin-3-yl)-pyrrolo[2,1-f][1,2,4]triazin-2-yl]-amine;

(±)-[4-(3,4-trans-3-Fluoro-piperidin-4-yl)-2-methoxy-phenyl]-[7-(2-methoxy-pyridin-3-yl)-pyrrolo[2,1-f][1,2,4]triazin-2-yl]-amine;

(3R,4S)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol;

(3S,4R)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol;

2-((3S,4S)-3-Fluoro-4-{3-methoxy-4-[7-(2-methoxy-phenyl)-pyrrolo[2,1-f][1,2,4]triazin-2-ylamino]-phenyl}-piperidin-1-yl)-ethanol;

2-((3R,4R)-3-Fluoro-4-{3-methoxy-4-[7-(2-methoxy-phenyl)-pyrrolo[2,1-f][1,2,4]triazin-2-ylamino]-phenyl}-piperidin-1-yl)-ethanol;

(3S,4S)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol;

(3R,4R)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol;

4-Bromo-benzoic acid 2-((3R,4R)-3-hydroxy-4-{3-methoxy-4-[7-(2-methoxy-phenyl)-pyrrolo[2,1-f][1,2,4]triazin-2-ylamino]-phenyl}-piperidin-1-yl)-ethyl ester;

2-(4-{3-Methoxy-4-[7-(2-methoxy-phenyl)-pyrrolo[2,1-f][1,2,4]triazin-2-ylamino]-phenyl}-piperidin-1-yl)-ethanol;

and/or a salt thereof.

In other embodiments, this application provides additional compounds that are isolated as single enantiomers, such as, for example,

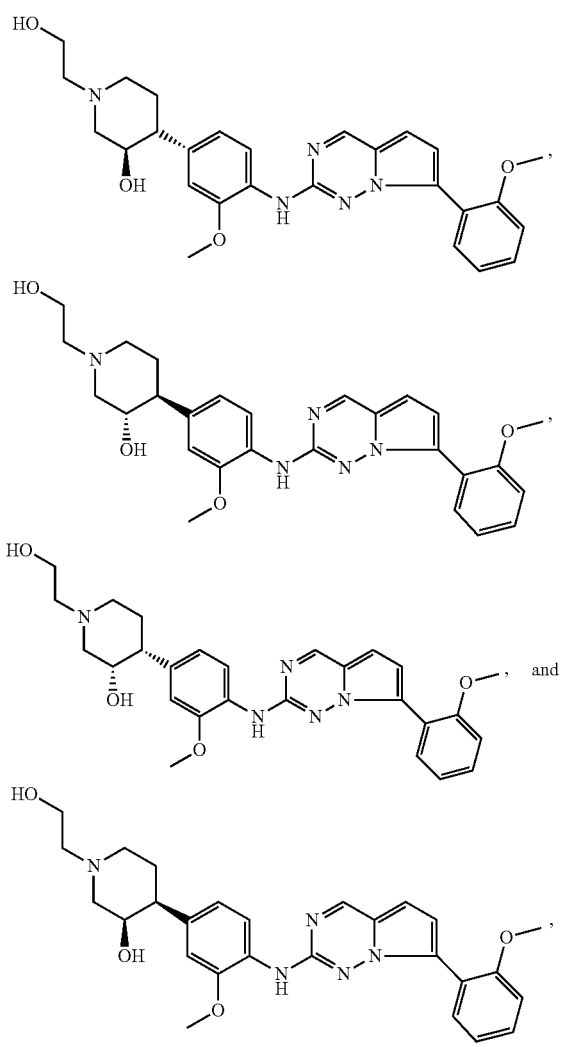

and/or a salt thereof.

This application also provides salts of the compounds described herein. Preferably, the salts are pharmaceutically acceptable. Pharmaceutically acceptable acid addition salts of the compounds of formula I include, but are not limited to, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such salts thus include, but are not limited to, sulfate, pyrosulfate, bisulfate, sulfite, bisulfate, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, and methanesulfonate. Also contemplated are the salts of amino acids such as arginate, gluconate, galacturonate, and the like; see, for example, Berge et al., "Pharmaceutical Salts," J. of Pharmaceutical Science, 1977; 66:1-19.

The acid addition salts of the basic compounds may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are in general equivalent to their respective free base for purposes of the present application.

Pharmaceutically acceptable base addition salts of compounds of formula I are formed with metals or amines, such as alkali and alkaline earth metal hydroxides, or of organic amines. Examples of metals used as cations include, but are not limited to, sodium, potassium, magnesium, and calcium. Examples of suitable amines include, but are not limited to, N,N'-dibenzylethylenediamine, chloroprocaine, choline, diethanolamine, ethylenediamine (ethane-1,2-diamine), N-methylglucamine, and procaine; see, for example, Berge et al., supra., 1977.

The base addition salts of acidic compounds may be prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are in general equivalent to their respective free acid for purposes of the present application.

III. Pharmaceutical Compositions

The present application further provides pharmaceutical compositions comprising a compound described herein (e.g., a compound of formula I or a pharmaceutically acceptable salt thereof, or any other compound described in this application including compounds depicted in the specification, examples or schemes), together with a pharmaceutically acceptable carrier, diluent, or excipient. The pharmaceutical composition may contain two or more compounds (i.e., two or more compounds may be used together in the pharmaceutical composition). Preferably, the pharmaceutical composition contains a therapeutically effective amount of at least one compound of the present application. In another embodiment, these compositions are useful in the treatment of an ALK-mediated disorder or condition. The compounds of the application can also be combined in a pharmaceutical composition that also comprises compounds that are useful for the treatment of cancer or another ALK-mediated disorder.

A compound of the present application can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present application will cause a decrease in symptoms or a disease indicia associated with an ALK mediated disorder as measured quantitatively or qualitatively.

For preparing a pharmaceutical composition using a compound of the present application, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component (i.e., compound of the present application). In tablets, the active component is mixed with the carrier having the necessary binding properties in suitable proportions and compacted in the shape and size desired.

The powders and tablets contain from 1% to 95% (w/w) of the active compound (i.e., compound of the present application). In another embodiment, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. The composition can, if desired, also contain other compatible therapeutic agents.

Pharmaceutically acceptable carriers are determined in part by the particular composition being administered, as well as by the particular method used to administer the composition. Accordingly, there is a wide variety of suitable formulations of pharmaceutical compositions of the present application (see, e.g., *Remington: The Science and Practice of Pharmacy*, 20th ed., Gennaro et al. Eds., Lippincott Williams and Wilkins, 2000).

A compound of the present application, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this application, compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

The dose administered to a subject, in the context of the present application should be sufficient to effect a beneficial therapeutic response in the subject over time. The dose will be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 10 mg/kg for a typical subject. Many different administration methods are known to those of skill in the art.

For administration, compounds of the present application can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

IV. Methods of Treatment

In another aspect, the present application provides a method of treating a subject suffering from an ALK-mediated disorder or condition comprising: administering to the subject a therapeutically effective amount of a compound of formula I or a pharmaceutically acceptable salt form thereof. In another aspect, the present application provides a compound of formula I or a pharmaceutically acceptable salt form thereof for use in treating a subject suffering from an ALK-mediated disorder or condition. Preferably, the compound of formula I or a pharmaceutically acceptable salt form thereof is administered to the subject in a pharmaceutical composition comprising a pharmaceutically acceptable carrier. In another aspect, the present application provides a pharmaceutical composition comprising a compound of formula I or a pharmaceutically acceptable salt form thereof for use in treating a subject suffering from an ALK-mediated disorder or condition. In another embodiment, the ALK mediated condition or disorder is cancer. In another embodiment, the ALK-mediated condition is selected from anaplastic large cell lymphoma, inflammatory myofibroblastic tumor, glioblastoma, and other solid tumors. In another embodiment, the ALK-mediated condition is selected from colon cancer, breast cancer, renal cancer, lung cancer, hemangioma, squamous cell myeloid leukemia, melanoma, glioblastoma, and astrocytoma.

The ALK-mediated disorder or condition can be treated prophylactically, acutely, and chronically using compounds of the present application, depending on the nature of the disorder or condition. Typically, the host or subject in each of these methods is human, although other mammals can also benefit from the administration of a compound of the present application.

In another embodiment, the present application provides a method of treating a proliferative disorder in a subject, comprising administering to the subject a therapeutically effective amount of a compound of formula I or a pharmaceutically acceptable salt form thereof. In another aspect, the present application provides a compound of formula I or a pharmaceutically acceptable salt form thereof for use in treating a proliferative disorder in a subject. Preferably, the compound of formula I or a pharmaceutically acceptable salt form thereof is administered to the subject in a pharmaceutical composition comprising a pharmaceutically acceptable carrier. In another aspect, the present application provides a pharmaceutical composition comprising a compound of formula I or a pharmaceutically acceptable salt form thereof for use in treating a proliferative disorder in a subject. In certain embodiments, the proliferative disorder is ALK mediated. In certain embodiments, the proliferative disorder is cancer. In certain embodiments, the proliferative disorder is selected from anaplastic large cell lymphoma, inflammatory myofibroblastic tumor, glioblastoma, and other solid tumors. In certain embodiments, the prolifereative disorder is selected from colon cancer, breast cancer, renal cancer, lung cancer, hemangioma, squamous cell myeloid leukemia, melanoma, glioblastoma, and astrocytoma.

The proliferative disorder can be treated prophylactically, acutely, and chronically using compounds of the present application, depending on the nature of the disorder or condition. Typically, the host or subject in each of these methods is human, although other mammals can also benefit from the administration of a compound of the present application.

The compounds of formula I share a common utility in treating ALK mediated disorders and a common core structure essential to that utility (i.e., the compounds of formula I are all pyrrolo[2,1-f][1,2,4]triazine derivatives).

In therapeutic applications, the compounds of the present application can be prepared and administered in a wide variety of oral and parenteral dosage forms. Thus, the compounds of the present application can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present application can be administered transdermally. In another embodiment, the compounds of the present application are delivered orally. The compounds can also be delivered rectally, bucally or by insufflation.

The compounds utilized in the pharmaceutical method of the application can be administered at the initial dosage of about 0.001 mg/kg to about 100 mg/kg daily. In another embodiment, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

V. Chemistry

Unless otherwise indicated, all reagents and solvents were obtained from commercial sources and used as received. $^1$H NMRs were obtained on a Bruker Avance at 400 MHz in the solvent indicated with tetramethylsilane as an internal standard. Analytical HPLC was run using a Zorbax RX-C8, 5×150 mm column eluting with a mixture of acetonitrile and water containing 0.1% trifluoroacetic acid with a gradient of 10-100%. LCMS results were obtained on either of two instruments. First, in Examples that indicate LCMS retention times, analysis was performed on a Waters Aquity Ultra Performance LC with a 2.1 mm×50 mm Waters Aquity UPLC BEH C18 1.7 μm column. The target column temperature was 45° C., with a run time of two (2) minutes, a flow rate of 0.600 mL/min, and a solvent mixture of 5% (0.1% formic acid/water):95% (acetonitrile/0.1% formic acid). The mass spectrometry data was acquired on a Micromass LC-ZQ 2000 quadrupole mass spectrometer. Second, in Examples that do not indicate LCMS retention times, analysis was performed on a Bruker Esquire 200 ion trap. Automated column chromatography was performed on a CombiFlash Companion (ISCO, Inc.). Melting points were taken on a Mel-Temp apparatus and are uncorrected.

Synthesis

The compounds of the present application can be prepared in a number of ways well known to one skilled in the art of organic synthesis. The compounds of the present application can be synthesized using the methods described below as well as using alternate methods known to one skilled in the art of organic chemistry including variations thereon as appreciated by those skilled in the art. The preferred methods include, but are not limited to or by, those described below. Unless otherwise stated, compounds are of commercial origin or readily synthesized by standard methods well known to one skilled in the art of organic synthesis.

The compounds of this application may be prepared using the reactions and techniques described in this section. The reactions are performed in solvents appropriate to the reagents, and materials employed are suitable for the transformations being effected. Also, in the description of the synthetic methods below, it is to be understood that all proposed reaction conditions, including choice of solvent, reaction atmosphere, reaction temperature, duration of experiment and workup procedures are chosen to be conditions standard for that reaction which should be readily recognized by one skilled in the art of organic synthesis.

It is understood that the examples and embodiments described herein are for illustrative purposes only and that various modifications or changes in light thereof will be suggested to persons skilled in the art and are to be included within the spirit and purview of this application and the scope of the appended claims. Specific chemical transformations are listed in the ensuing schemes and one skilled in the art appreciates that a variety of different reagents may be used in place of those listed. Common replacements for such reagents can be found in, but not limited to, texts such as "Encyclopedia of Reagents for Organic Synthesis" Leo A. Paquette, John Wiley & Son Ltd (1995) or "Comprehensive Organic Transformations: A Guide to Functional Group Preparations" Richard C. Larock. Wiley-VCH and "Strategic Applications of Named Reactions in Organic Synthesis" Kurti and Czako, Elsevier, 2005 and references therein.

General Reaction Schemes.

The synthesis of Examples 1, 2, 4, and 14 followed the general reaction sequence depicted in the general Scheme 1:

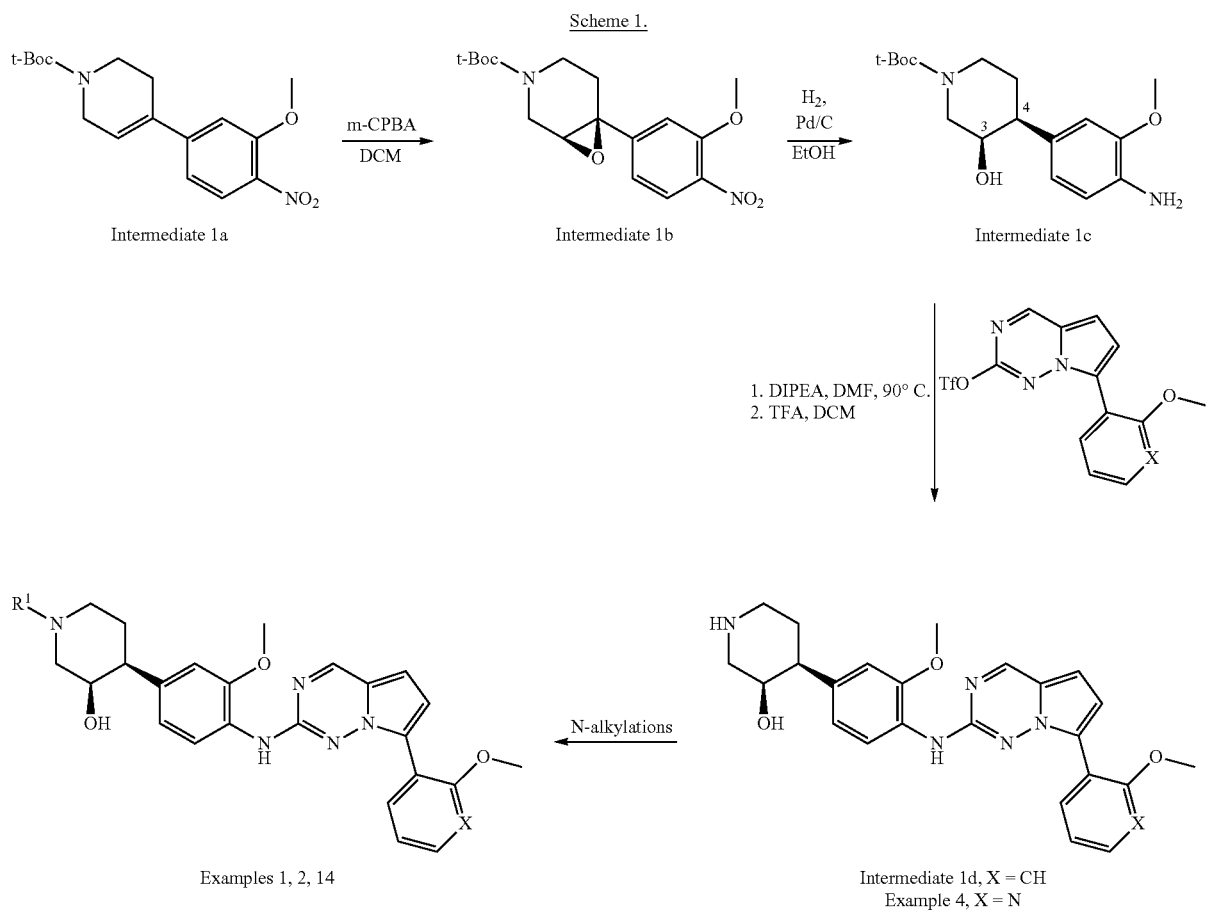
The synthesis of Examples 3, 5, 8, 10, and 13 followed the general reaction sequence depicted in the general Scheme 2:
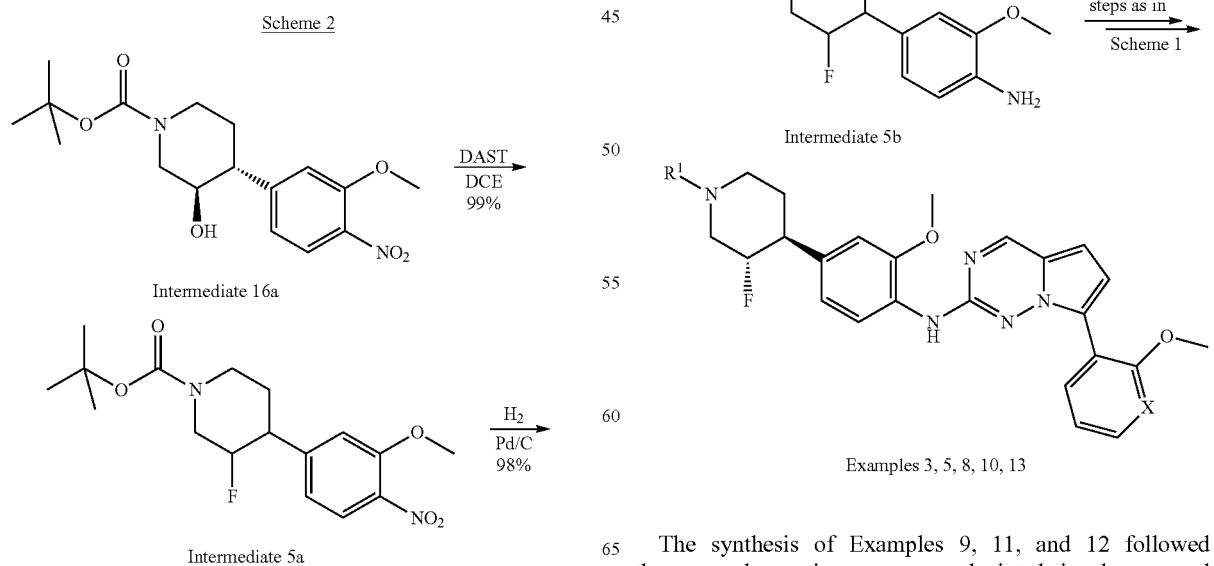
The synthesis of Examples 9, 11, and 12 followed the general reaction sequence depicted in the general Scheme 3:

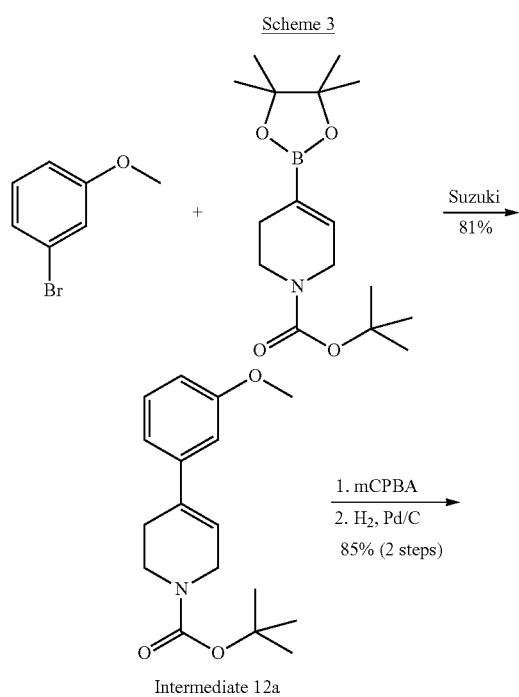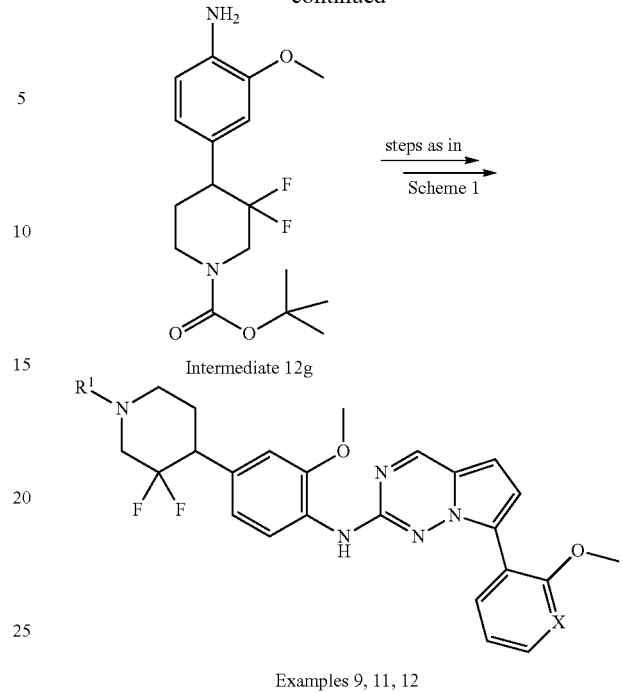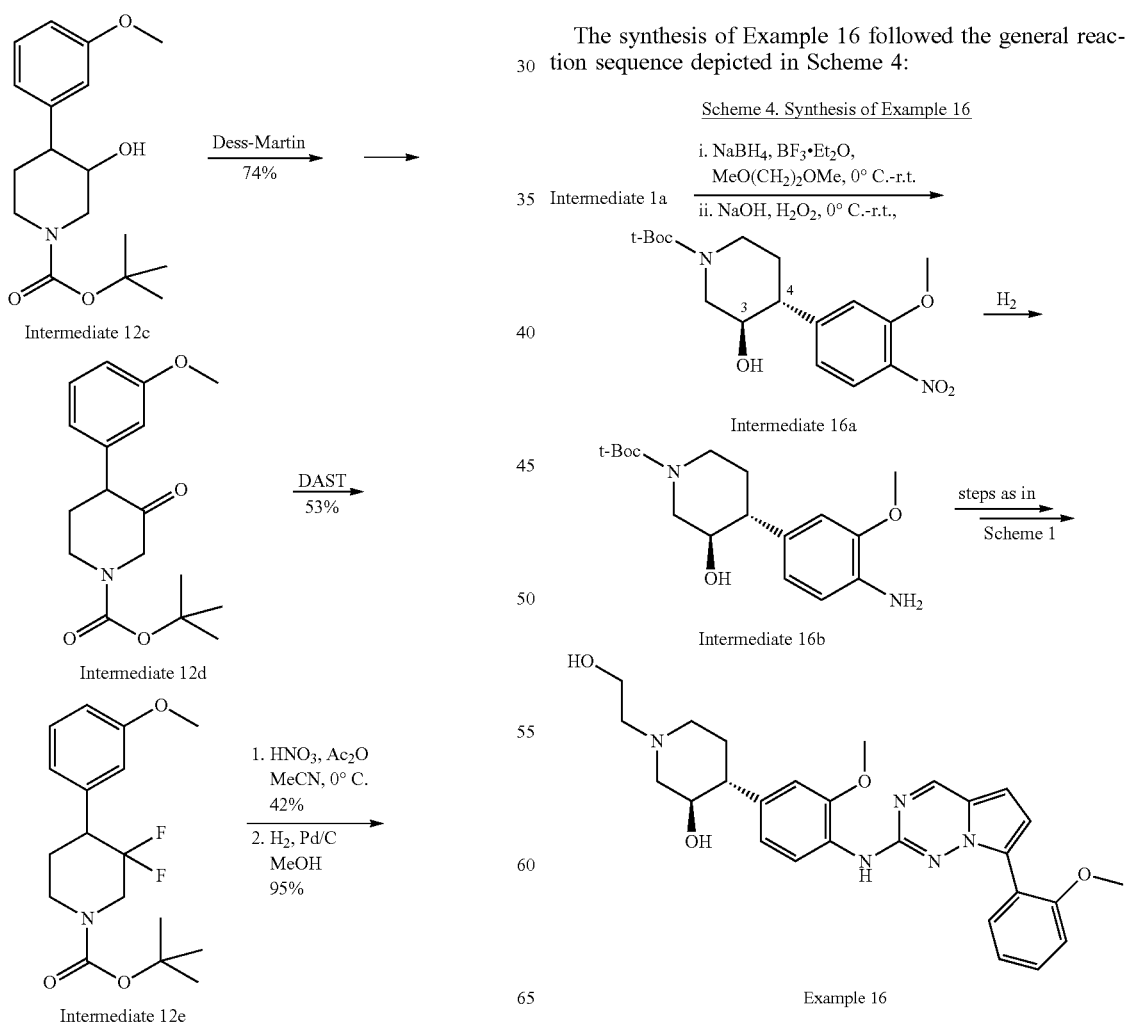
The synthesis of Example 16 followed the general reaction sequence depicted in Scheme 4:

The synthesis of Example 17 from Example 16b followed the reaction sequence outlined in Scheme 5:

Scheme 5. Synthesis of Example 17

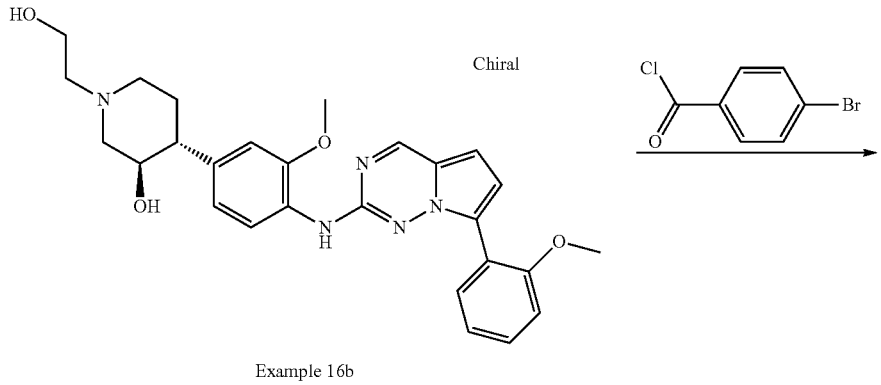

Example 16b

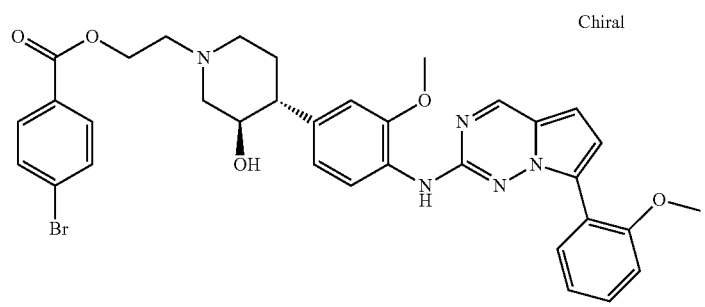

Example 17

EXPERIMENTAL PROCEDURES

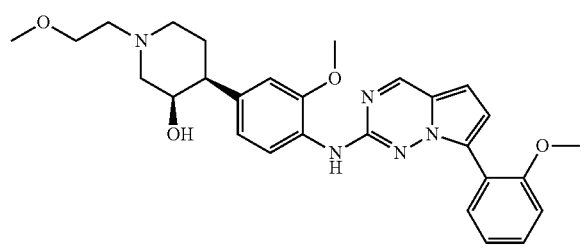

Example 1

(±)-3,4-cis-1-(2-Methoxy-ethyl)-4-{3-methoxy-4-[7-(2-methoxy-phenyl)-pyrrolo[2,1-f][1,2,4]triazin-2-ylamino]-phenyl}-piperidin-3-ol 1a) 4-Chloro-2-methoxy-1-nitro-benzene (1.12 g, 5.96 mmol), 4-(4,4,5,5-tetramethyl-[1,3,2]dioxaborolan-2-yl)-3,6-dihydro-2H-pyridine-1-carboxylic acid tert-butyl ester (1.84 g, 5.95 mmol), tetrakis(triphenylphosphine)palladium (0) (380 mg, 0.33 mmol), a 2 M solution of potassium bicarbonate in water (7.45 mL, 14.9 mmol), and 1,4-dioxane (18 mL) were combined in a sealed tube, and the mixture was stirred and heated at 80° C. overnight. HPLC indicated the complete conversion of the starting material. The product, 4-(3-methoxy-4-nitro-phenyl)-3,6-dihydro-2H-pyridine-1-carboxylic acid tert-butyl ester was isolated by flash chromatography (Silicagel, EtOAc/Hexanes 25-50%) in 90% yield.

1d) 4-(3-methoxy-4-nitro-phenyl)-3,6-dihydro-2H-pyridine-1-carboxylic acid tert-butyl ester, Intermediate 1a, was converted to (±)-(3R,4S)-4-{3-methoxy-4-[7-(2-methoxy-phenyl)-pyrrolo[2,1-f][1,2,4]triazin-2-ylamino]-phenyl}-piperidin-3-ol (intermediate 1d) as outlined in Scheme 1 and described in detail in U.S. Pat. No. 8,471,005 (Appl. WO2010071885).

1e) A mixture of (±)-(3R,4S)-4-{3-Methoxy-4-[7-(2-methoxy-phenyl)-pyrrolo[2,1-f][1,2,4]triazin-2-ylamino]-phenyl}-piperidin-3-ol (intermediate 1d, prepared as described in U.S. Pat. No. 8,471,005/Appl. WO2010071885; 60 mg, 0.13 mmol), 1-bromo-2-methoxy-ethane, (26 mg, 0.19 mmol), and sodium bicarbonate (13.6 mg, 0.16 mmol) in acetonitrile (1.5 mL) was heated to reflux overnight, then the solvent was evaporated under vacuum and the title product was isolated by preparative reverse phase hplc (on Gilson) as a yellow foam (14.5 mg, 21.4% yield). $^1$H NMR (CDCl3): 8.68 (s, 1H), 8.30 (d, J=8.3 Hz, 1H), 7.99 (d, J=7.6 Hz, 1H), 7.46 (br s, 1H), 7.42 (m, 1H), 7.12 (m, 1H), 7.06 (d, J=8.3 Hz, 1H), 7.01 (d, J=4.1 Hz, 1H), 6.89 (s, 1H), 6.83 (d, J=4.1 Hz, 1H), 6.78 (d, J=8.2 Hz, 1H), 3.90 (br s, 1H), 3.89 (s, 3H), 3.84 (s, 3H), 3.54 (m, 2H), 3.36 (s, 3H), 3.13 (m, 1H), 3.06 (m, 1H), 2.64 (m, 4H), 2.35 (d, J=11.4 Hz, 1H), 2.22 (br s, 2H), 1.68 (m, 1H); LC/MS (ESI+): 504.1 (M+H).

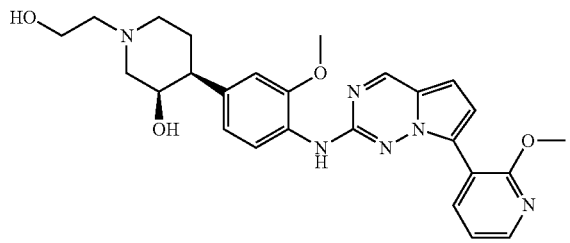

Example 2

(±)-3,4-cis-1-(2-Hydroxy-ethyl)-4-{3-methoxy-4-[7-(2-methoxy-pyridin-3-yl)-pyrrolo[2,1-f][1,2,4]triazin-2-ylamino]-phenyl}-piperidin-3-ol Ethylene oxide (40 mg, 0.9 mmol) was trapped in a glass tube at −78° C. and then (±)-(3R,4S)-4-{3-Methoxy-4-[7-(2-methoxy-pyridin-3-yl)-pyrrolo[2,1-f][1,2,4]triazin-2-ylamino]-phenyl}-piperidin-3-ol (Example 4; 40 mg, 0.09 mmol) in tetrahydrofuran (200 μL) was added at the same temperature and the tube was capped and the reaction was allowed to stir overnight at room temperature. The volatiles were then evaporated under reduced pressure and the product was isolated by (Isco) flash column chromatography (DCM/MeOH on Silicagel) to afford the product as a yellow foam (25 mg, 57% yield). $^1$H NMR (CDCl$_3$): 8.70 (s, 1H), 8.48 (d, J=7.6 Hz, 1H), 8.24 (d, J=8.1 Hz, 1H), 7.47 (br s, 1H), 7.13 (d, J=4.1 Hz, 1H), 7.07 (m, 2H), 6.88 (s, 1H), 6.82 (m, 2H), 4.02 (s, 3H), 3.96 (br s, 1H), 3.90 (s, 3H), 3.70 (m, 2H), 3.11 (m, 2H), 2.64 (m, 3H), 2.38 (d, J=11.5 Hz, 1H), 2.22 (m, 4H), 1.72 (d, J=11.5 Hz, 1H); LC/MS (ESI+): 491.0 (M+H)

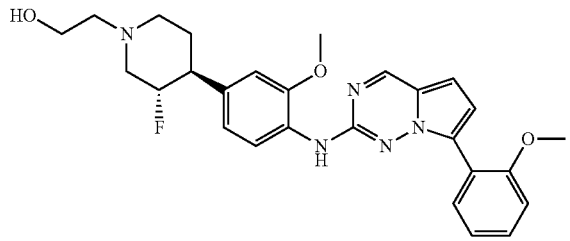

Example 3

(±)-2-(3,4-trans-3-Fluoro-4-{3-methoxy-4-[7-(2-methoxy-phenyl)-pyrrolo[2,1-f][1,2,4]triazin-2-ylamino]-phenyl}-piperidin-1-yl)-ethanol (±)-[4-(3,4-Trans-3-fluoro-piperidin-4-yl)-2-methoxy-phenyl]-[7-(2-methoxy-phenyl)-pyrrolo[2,1-f][1,2,4]triazin-2-yl]-amine (Example 5; 55 mg, 0.12 mmol) was converted to the title product by a procedure similar to the one described for Example 2 to give a yellow foam (35 mg, 58% yield). $^1$H NMR (CDCl$_3$): 8.69 (s, 1H), 8.34 (d, J=8.0 Hz, 1H), 7.98 (d, J=7.6 Hz, 1H), 7.48 (s, 1H), 7.44 (m, 1H), 7.14 (m, 1H), 7.07 (d, J=8.3 Hz, 1H), 7.02 (d, J=4.1 Hz, 1H), 6.84 (d, J=4.1 Hz, 1H), 6.77 (m, 2H), 4.63 (dddd, J=48.4; 9.7; 9.7; 4.6 Hz, 1H), 3.90 (s, 3H), 3.84 (s, 3H), 3.67 (m, 2H), 3.35 (m, 1H), 2.96 (d, J=11.4 Hz, 1H), 2.65 (m, 3H), 2.55 (br s, 1H; —OH), 2.19 (m, 2H), 1.86 (m, 2H); LC/MS (ESI+): 492.0 (M+H).

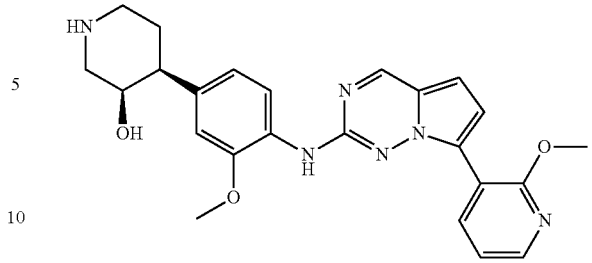

Example 4

(±)-3,4-cis-4-{3-Methoxy-4-[7-(2-methoxy-pyridin-3-yl)-pyrrolo[2,1-f][1,2,4]triazin-2-ylamino]-phenyl}-piperidin-3-ol Into a 8-dram vial, 7-(2-methoxy-pyridin-3-yl)-pyrrolo[2,1-f][1,2,4]triazin-2-ol (prepared as described in U.S. Pat. No. 8,471,005/Appl. WO2010071885; 70 mg, 0.29 mmol), N,N-dimethylformamide (1 mL, 13 mmol), N,N-diisopropylethylamine (0.15 mL) and N-phenylbis(trifluoromethanesulphonimide) (124 mg, 0.35 mmol) were added. The reaction mixture was stirred at room temperature for one hour. (±)-(3R,4S)-4-(4-Amino-3-methoxy-phenyl)-3-hydroxy-piperidine-1-carboxylic acid tert-butyl ester (Intermediate 12P prepared as described in Scheme 2 and in U.S. Pat. No. 8,471,005/Appl. WO2010071885; 111.8 mg, 0.35 mmol) was added. The reaction was heated at 80° C. overnight. The reaction mixture was partitioned between EtOAc and aqueous sodium bicarbonate, the organic extracts were dried (MgSO$_4$) and the solvent was evaporated under reduced pressure. The crude residue was taken in methylene chloride (1 mL) and treated with trifluoroacetic acid (0.45 mL, 5.78 mmol) at room temperature until HPLC indicated complete removal of the Boc group. The reaction mixture was concentrated under vacuum and the product was isolated by reverse-phase pre-hplc (Gilson) followed by free base isolation by work-up on catch/release acid-resin (Strata/Phenomenex) to provide the product as a yellow foam (82.00 mg, 63.5%). $^1$H NMR (CDCl$_3$): 8.72 (s, 1H), 8.48 (d, J=7.6 Hz, 1H), 8.25 (m, 2H), 7.48 (s, 1H), 7.14 (d, J=4.1 Hz, 1H), 7.08 (m, 1H), 6.83 (m, 4H), 4.02 (s, 3H), 3.92 (s, 3H), 3.88 (br s, 1H), 3.24 (m, 2H), 2.89 (d, J=12.6 Hz, 1H), 2.76 (m, 2H), 2.17 (m, 2H), 1.64 (d, J=12.6 Hz, 1H); LC/MS (ESI+): 447.0 (M+H).

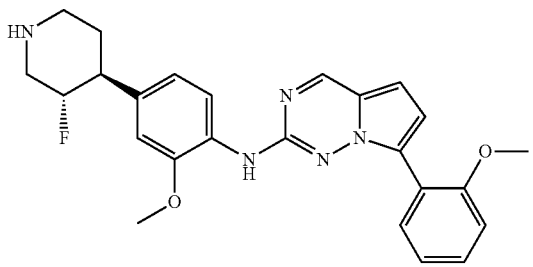 [SMILES: COc1cc([C@@H]2CCNC[C@H]2F)ccc1Nc1ncc2ccc(-c3ccccc3OC)n2n1]

Example 5

(±)-[4-(3,4-trans-3-Fluoro-piperidin-4-yl)-2-methoxy-phenyl]-[7-(2-methoxy-phenyl)-pyrrolo[2,1-f][1,2,4]triazin-2-yl]-amine 5a). A solution of (±)-3,4-trans-3-hydroxy-4-(3-methoxy-4-nitro-phenyl)-piperidine-1-carboxylic acid tert-butyl ester (Intermediate 16a, prepared as described in Scheme 4 and in U.S. Pat. No. 8,471,005/Appl. WO2010071885; 200 mg, 0.57 mmol) in 1,2-dichloroethane (6 mL) was treated with diethylaminosulfur trifluoride (188 uL, 1.42 mmol) at ~0° C., and the reaction mixture was stirred overnight, allowing it to warm to room temperature. The reaction mixture was quenched with dilute aq. NaHCO$_3$, and the product extracted with DCM. The organic extracts were washed once with water, dried (MgSO$_4$), then filtered, and the solvent was evaporated under reduced pressure to afford the crude product, (±)-3-fluoro-4-(3-methoxy-4-nitro-phenyl)-piperidine-1-carboxylic acid tert-butyl ester (200 mg, 99% yield), which was used without purification. $^1$H NMR (CDCl$_3$): δ ppm 7.86 (d, J=8.1 Hz, 1H), 6.87-7.00 (m, 2H), 4.58 (br. s., 2H), 4.13-4.32 (m, 1H), 3.98 (s, 3H), 2.70-2.92 (m, 3H), 1.93 (d, J=13.6 Hz, 1H), 1.68-1.83 (m, 1H), 1.49 (s, 9H).

5b). To a solution of (±)-3-fluoro-4-(3-methoxy-4-nitro-phenyl)-piperidine-1-carboxylic acid tert-butyl ester in methanol (10 mL) was added palladium on carbon 10% (1:9 palladium:carbon black, 40 mg). The mixture was shaken in a Parr apparatus under an atmosphere of hydrogen (35 PSI) overnight. Filtration through Celite and evaporation of the solvent provided crude (±)-4-(4-amino-3-methoxy-phenyl)-3-fluoro-piperidine-1-carboxylic acid tert-butyl ester (180 mg, 98%), which was used without purification. $^1$H NMR (CDCl$_3$): δ ppm 6.63-6.71 (m, 3H), 4.52 (br. s., 2H), 4.05-4.26 (m, 1H), 3.85 (s, 3H), 3.74 (br. s., 2H), 2.63-2.86 (m, 3H), 1.88 (d, J=13.4 Hz, 1H), 1.62-1.79 (m, 1H), 1.49 (s, 9H).

5c) 7-(2-Methoxy-phenyl)-pyrrolo[2,1-f][1,2,4]triazin-2-ol (prepared as described in U.S. Pat. No. 8,471,005/Appl. WO2010071885; 120 mg, 0.50 mmol) and (±)-3,4-trans-4-(4-amino-3-methoxy-phenyl)-3-fluoro-piperidine-1-carboxylic acid tert-butyl ester (194 mg, 0.6 mmol) were converted to the title product by a procedure similar to the one described for Example 4: yellow foam (111.00 mg, 50% yield). $^1$H NMR (CDCl$_3$): 8.69 (s, 1H), 8.35 (d, J=8.2 Hz, 1H), 7.98 (d, J=7.6 Hz, 1H), 7.47 (s, 1H), 7.43 (m, 1H), 7.13 (m, 1H), 7.07 (d, J=8.3 Hz, 1H), 7.02 (d, J=4.3 Hz, 1H), 6.84 (d, J=4.3 Hz, 1H), 6.82 (m, 2H), 4.56 (dddd, J=48.5; 9.7; 9.7; 5.0 Hz, 1H), 3.90 (s, 3H), 3.84 (s, 3H), 3.48 (d, J=11.3 Hz, 1H), 3.08 (d, J=11.8 Hz, 1H), 2.68 (m, 3H), 1.92 (m, 1H), 1.76 (m, 2H); LC/MS (ESI+):448.0 (M+H).

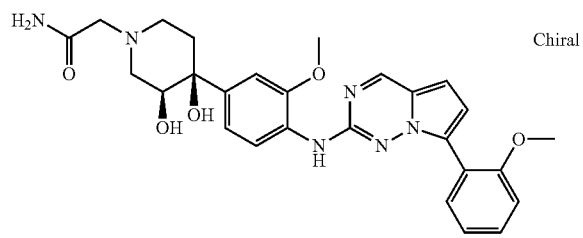

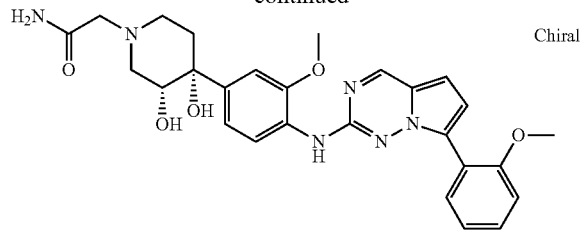

Examples 6 and 7

2-((3S,4S)-3,4-Dihydroxy-4-{3-methoxy-4-[7-(2-methoxy-phenyl)-pyrrolo[2,1-f][1,2,4]triazin-2-ylamino]-phenyl}-piperidin-1-yl)-acetamide and 2-((3R,4R)-3,4-Dihydroxy-4-{3-methoxy-4-[7-(2-methoxy-phenyl)-pyrrolo[2,1-f][1,2,4]triazin-2-ylamino]-phenyl}-piperidin-1-yl)-acetamide Enantiomerically pure Examples 6 and 7 were prepared by chromatographic separation from racemic (±)-2-(3,4-cis-3,4-dihydroxy-4-{3-methoxy-4-[7-(2-methoxy-phenyl)-pyrrolo[2,1-f][1,2,4]triazin-2-ylamino]-phenyl}-piperidin-1-yl)-acetamide (exemplified in U.S. Pat. No. 8,471,005/Appl. WO2010071885) by a SFC procedure similar to the one described for Examples 16a and 16b. Example 6 (ee>99%) is first to elute from the column, and Example 7 is the second to elute from the column (ee>99%).

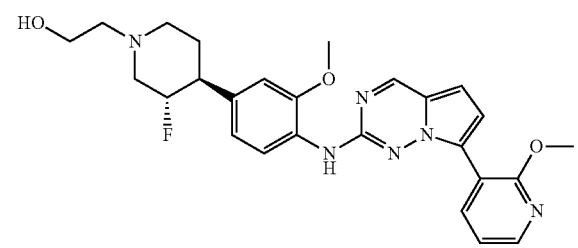 [SMILES: COc1cc([C@@H]2CCN(CCO)C[C@H]2F)ccc1Nc1ncc2ccc(-c3cccnc3OC)n2n1]

Example 8

(±)-2-(3,4-trans-3-fluoro-4-{3-methoxy-4-[7-(2-methoxy-pyridin-3-yl)-pyrrolo[2,1-f][1,2,4]triazin-2-ylamino]-phenyl}-piperidin-1-yl)-ethanol Ethylene oxide and (±)-[4-(3,4-trans-3-Fluoro-piperidin-4-yl)-2-methoxy-phenyl]-[7-(2-methoxy-pyridin-3-yl)-pyrrolo[2,1-f][1,2,4]triazin-2-yl]-amine (Example 13, 60 mg) in methanol (0.4 mL) were converted to the title product by a procedure similar to the one described for Example 2, but at 50° C., to give a yellow foam (34 mg, 52% yield). $^1$H NMR (CDCl$_3$): 8.72 (s, 1H), 8.48 (d, J=7.5 Hz, 1H), 8.29 (d, J=8.2 Hz, 1H), 8.25 (m, 1H), 7.49 (br s, 1H), 7.14 (d, J=3.2 Hz, 1H), 7.08 (m, 1H), 6.82 (m, 3H), 4.65 (dddd, J=48 (H-F coupling), 11.2, 11.2, 3.4 Hz, 1H), 4.02 (s, 3H), 3.92 (s, 3H), 3.68 (m, 2H), 3.36 (m, 1H), 2.98 (d, J=11.0 Hz, 1H), 2.67 (m, 3H), 2.22 (m, 3H), 1.92 (m, 1H), 1.84 (m, 1H); LC/MS (ESI+): 493.0 (M+H).

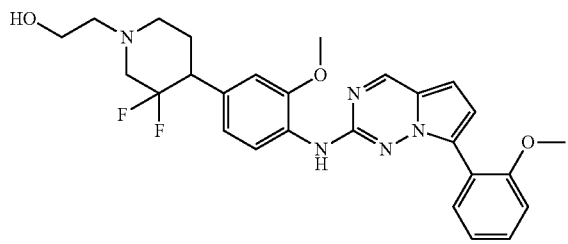 [SMILES: COc1cc(C2CCN(CCO)CC2(F)F)ccc1Nc1ncc2ccc(-c3ccccc3OC)n2n1]

Example 9

(±)-2-(3,3-Difluoro-4-{3-methoxy-4-[7-(2-methoxy-phenyl)-pyrrolo[2,1-f][1,2,4]triazin-2-ylamino]-phenyl}-piperidin-1-yl)-ethanol (±)-[4-(3,3-Difluoro-piperidin-4-yl)-2-methoxy-phenyl]-[7-(2-methoxy-phenyl)-pyrrolo[2,1-f][1,2,4]triazin-2-yl]-amine (prepared in a manned similar to Example 12; 68 mg, 0.15 mmol) was converted to the title product by a procedure similar to the one described for Example 8 to give a yellow foam (47 mg, 63% yield). $^1$H NMR (CDCl$_3$): 8.70 (s, 1H), 8.34 (d, J=8.2 Hz, 1H), 7.97 (d, J=7.6 Hz, 1H), 7.50 (s, 1H), 7.43 (m, 1H), 7.13 (m, 1H), 7.07 (d, J=8.3 Hz, 1H), 7.02 (d, J=4.2 Hz, 1H), 6.82 (m, 3H), 3.91 (s, 3H), 3.84 (s, 3H), 3.68 (m, 2H), 3.24 (m, 1H), 3.09 (m, 1H), 2.87 (m, 1H), 2.68 (m, 2H), 2.45 (dd, J=28.2 (F-H vicinal coupling), 11.6 Hz, 1H), 2.27 (m, 3H), 1.89 (m, 1H); LC/MS (ESI+): 509.9 (M+H).

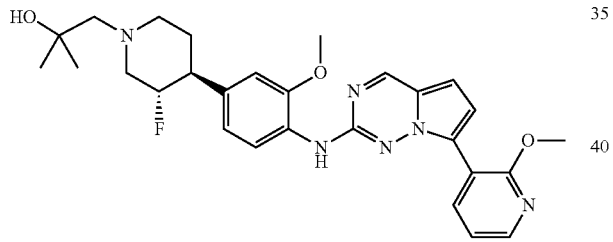

Example 10

(±)-1-(3,4-trans-3-Fluoro-4-{3-methoxy-4-[7-(2-methoxy-pyridin-3-yl)-pyrrolo[2,1-f][1,2,4]triazin-2-ylamino]-phenyl}-piperidin-1-yl)-2-methyl-propan-2-ol 1,2-Epoxy-2-methylpropane and (±)-[4-(3,4-trans-3-fluoro-piperidin-4-yl)-2-methoxy-phenyl]-[7-(2-methoxy-pyridin-3-yl)-pyrrolo[2,1-f][1,2,4]triazin-2-yl]-amine (Example 13, 58 mg) were converted to the title product by a procedure similar to the one described for Example 8 to give a yellow foam (36 mg, 53% yield). $^1$H NMR (CDCl$_3$): 8.71 (s, 1H), 8.48 (d, J=7.4 Hz, 1H), 8.28 (d, J=8.2 Hz, 1H), 8.26 (d, J=4.5 Hz, 1H), 7.49 (s, 1H), 7.13 (d, J=4.5 Hz, 1H), 7.10 (m, 1H), 6.84 (d, J=4.5 Hz, 1H), 6.79 (m, 2H), 4.64 (dddd, J=48.3 (F-H gem. coupling), 9.8, 9.8, 4.3 Hz, 1H), 4.02 (s, 3H), 3.93 (s, 3H), 3.36 (m, 1H), 2.96 (m, 1H), 2.86 (br s, 1H), 2.60 (m, 1H), 2.47 (m, 4H), 1.87 (m, 2H), 1.22 (s, 3H), 1.21 (s, 3H); LC/MS (ESI+): 521.0 (M+H).

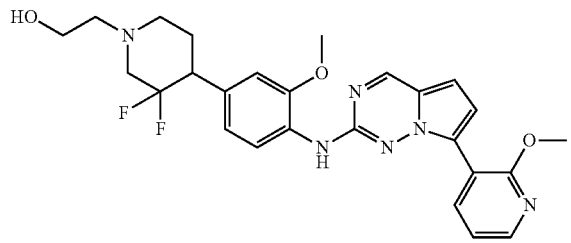

Example 11

(±)-2-(3,3-Difluoro-4-{3-methoxy-4-[7-(2-methoxy-pyridin-3-yl)-pyrrolo[2,1-f][1,2,4]triazin-2-ylamino]-phenyl}-piperidin-1-yl)-ethanol Ethylene oxide and (±)-[4-(3,3-difluoro-piperidin-4-yl)-2-methoxy-phenyl]-[7-(2-methoxy-pyridin-3-yl)-pyrrolo[2,1-f][1,2,4]triazin-2-yl]-amine (Example 12, 68 mg) were converted to the title product by a procedure similar to the one described for Example 8 to give a yellow foam (51 mg, 68% yield). $^1$H NMR (CDCl$_3$): 8.72 (s, 1H), 8.48 (d, J=7.4 Hz, 1H), 8.28 (d, J=8.1 Hz, 1H), 8.24 (d, J=4.3 Hz, 1H), 7.51 (s, 1H), 7.14 (d, J=3.6 Hz, 1H), 7.08 (m, 1H), 6.84 (m, 2H), 4.02 (s, 3H), 3.92 (s, 3H), 3.68 (m, 2H), 3.25 (m, 1H), 3.10 (m, 1H), 2.90 (m, 1H), 2.74 (m, 1H), 2.65 (m, 1H), 2.46 (dd, J=28.3 (F-H vic. coupling), 11.7 Hz, 1H), 2.27 (m, 3H), 1.90 (m, 1H); LC/MS (ESI+): 510.54 (M+H).

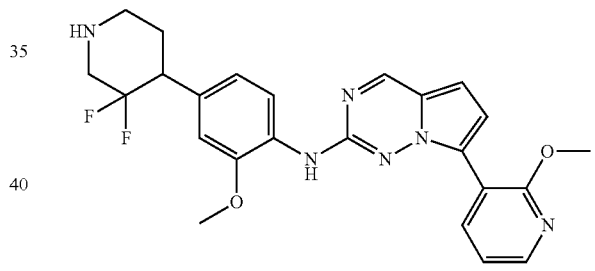

Example 12

(±)-[4-(3,3-Difluoro-piperidin-4-yl)-2-methoxy-phenyl]-[7-(2-methoxy-pyridin-3-yl)-pyrrolo[2,1-f][1,2,4]triazin-2-yl]-amine 12a). 1-Bromo-3-methoxy-benzene (10 g, 53.5 mmol), 4-(4,4,5,5-tetramethyl-[1,3,2]dioxaborolan-2-yl)-3,6-dihydro-2H-pyridine-1-carboxylic acid tert-butyl ester (16.5 g, 53.5 mmol), tetrakis(triphenylphosphine)palladium(0) (3.1 g, 2.7 mmol), a solution of 2 M sodium carbonate in water (67 mL, 133.7 mmol), were combined in 1,4-dioxane (150 mL) in a round bottom flask, and the mixture was heated at 80° C. overnight. The product was isolated by flash chromatography (Silicagel, EtOAc/Hexanes) to afford 4-(3-Methoxy-phenyl)-3,6-dihydro-2H-pyridine-1-carboxylic acid tert-butyl ester (12.5 g, 81% yield). $^1$H NMR (CDCl$_3$): 7.26 (m, 1H), 6.97 (d, J=7.6 Hz, 1H), 6.91 (s, 1H), 6.81 (d, J=8.1 Hz, 1H), 6.04 (br. s., 1H), 4.07 (br. s., 2H), 3.82 (s, 3H), 3.60-3.68 (m, 2H), 2.52 (br. s., 2H), 1.49 (s, 9H).

12b). 4-(3-Methoxy-phenyl)-3,6-dihydro-2H-pyridine-1-carboxylic acid tert-butyl ester (2 g, 6.9 mmol) was further purified by flash chromatography (100 DCM on Silicagel) to remove baseline impurities (likely waste palladium from Suzuki reaction), then was dissolved in methylene chloride (28.9 mL, 451 mmol) and treated with m-CPBA 70-75% (70:30, m-chloroperbenzoic acid: 3-chlorobenzoic acid, 2.4 g, 9.7 mmol) at room temperature overnight. The reaction was quenched by treatment with a $Na_2S_2O_3$ aq solution, followed by sat. $NaHCO_3$ aq. solution, and further extracted twice with dichloromethane. The combined organic extracts were dried ($MgSO_4$) and filtered, and the solvent was evaporated under reduce pressure. The product was used without further purification in the next step: (±)-6-(3-methoxy-phenyl)-7-oxa-3-aza-bicyclo[4.1.0]heptane-3-carboxylic acid tert-butyl ester (2 g, 95% yield). $^1$H NMR ($CDCl_3$): δ ppm 7.26 (m, 1H), 6.95 (d, J=7.8 Hz, 1H), 6.90 (br. s., 1H), 6.84 (d, J=8.1 Hz, 1H), 3.93-4.19 (m, 1H), 3.81 (s, 3H), 3.53-3.79 (m, 2H), 3.10-3.24 (m, 2H), 2.38-2.51 (m, 1H), 2.17 (br. s., 1H), 1.48 (s, 9H).

12c). To a solution of (±)-6-(3-methoxy-phenyl)-7-oxa-3-aza-bicyclo[4.1.0]heptane-3-carboxylic acid tert-butyl ester (2 g) in methanol (115 mL) was added palladium on carbon 10% (10:90, palladium:carbon black, 400 mg). The mixture was shaken in a Parr apparatus under an atmosphere of hydrogen (50 PSI) overnight. Filtration through Celite and evaporation of the solvent provided the crude product. The product was purified by flash chromatography (Silicagel, EtOAc/hexanes) to give (±)-3-hydroxy-4-(3-methoxy-phenyl)-piperidine-1-carboxylic acid tert-butyl ester (1.79 g, 89% yield). $^1$H NMR ($CDCl_3$): δ ppm 7.26 (s, 1H), 6.72-6.92 (m, 3H), 4.31 (br. s., 2H), 3.96 (br. s., 1H), 3.81 (s, 3H), 3.01 (d, J=13.4 Hz, 1H), 2.70-2.92 (m, 2H), 2.13-2.34 (m, 1H), 1.64 (br. s., 2H), 1.49 (s, 9H).

12d). (±)-3-Hydroxy-4-(3-methoxy-phenyl)-piperidine-1-carboxylic acid tert-butyl ester (1.27 g, 4.13 mmol) and pyridine (334 uL, 4 mmol) in methylene chloride (70 mL) at 0° C. were treated with Dess-Martin periodinane (3.5 g, 8.3 mmol) and then the reaction was stirred at room temperature for 2 h. The reaction was quenched by addition of a mixture of sat. solution of $Na_2S_2O_3$ and sat. solution of $NaHCO_3$ (1:1 v:v) (50 ml), which was followed by extraction with ether. The product was isolated by flash chromatography to afford (±)-4-(3-methoxy-phenyl)-3-oxo-piperidine-1-carboxylic acid tert-butyl ester (0.94 g, 75% yield). $^1$H NMR ($CDCl_3$): δ ppm 7.27 (m, 1H), 6.83 (d, J=8.1 Hz, 1H), 6.70-6.75 (m, 1H), 6.68 (s, 1H), 4.24 (d, J=18.2 Hz, 1H), 4.06 (d, J=18.2 Hz, 2H), 3.80 (s, 3H), 3.62 (dd, J=11.5, 5.9 Hz, 1H), 3.51 (br. s., 1H), 2.19-2.35 (m, 2H), 1.44-1.53 (m, 9H).

12e). A solution of (±)-4-(3-methoxy-phenyl)-3-oxo-piperidine-1-carboxylic acid tert-butyl ester (900 mg, 2.95 mmol) in 1,2-dichloroethane (50 mL) was treated with diethylaminosulfur trifluoride (974 uL, 7.4 mmol) at ~0° C., and the reaction mixture was stirred overnight, allowing it to warm to room temperature. The reaction mixture was quenched with dilute aq. $NaHCO_3$, and the product was extracted with DCM. The organic extracts were washed once with water, dried ($MgSO_4$) and filtered, then the solvent was evaporated under reduced pressure. The crude product was used without purification: (±)-3,3-difluoro-4-(3-methoxy-phenyl)-piperidine-1-carboxylic acid tert-butylester (515 mg, 53% yield). $^1$H NMR ($CDCl_3$): δ ppm 7.22-7.30 (m, 1H), 6.89 (d, J=7.6 Hz, 1H), 6.86 (br. s., 2H), 4.13-4.67 (m, 2H), 3.81 (s, 3H), 2.92-3.17 (m, 2H), 2.83 (br. s., 1H), 2.09-2.24 (m, 1H), 1.87 (d, J=12.4 Hz, 1H), 1.49 (s, 9H).

12f). Nitric acid (77 uL, 1.8 mmol) was added to acetic anhydride (865 uL, 9.2 mmol) at 0° C. under an atmosphere of nitrogen and the mixture was stirred for 5-10 min. The resulting solution was added to a solution of (±)-3,3-difluoro-4-(3-methoxy-phenyl)-piperidine-1-carboxylic acid tert-butyl ester (500 mg, 1.5 mmol) in acetonitrile (12 mL) at 0° C. under an atmosphere of nitrogen, and the reaction was stirred for 2 hours at this temperature. Cold DCM was added, then the reaction was quenched with sat. aq. $NaHCO_3$. The organic extracts were dried ($MgSO_4$), filtered, and concentrated under reduced pressure. The desired regioisomer product was isolated by flash chromatography (ISCO, Silicagel, EtOAc/Hexanes 1:4) to afford the (±)-3,3-difluoro-4-(3-methoxy-4-nitro-phenyl)-piperidine-1-carboxylic acid tert-butyl ester (240 mg, 42% yield) as a white foamy solid. $^1$H NMR and NOEDiff ($CDCl_3$): δ ppm 7.84 (d, J=8.3 Hz, 1H), 7.02 (s, 1H), 6.97 (d, J=8.3 Hz, 1H), 4.42 (br. s., 2H), 3.97 (s, 3H), 2.73-3.20 (m, 3H), 2.09-2.27 (m, 1H), 1.91 (d, J=14.1 Hz, 1H), 1.50 (s, 9H).

12g). To a solution of (±)-3,3-difluoro-4-(3-methoxy-4-nitro-phenyl)-piperidine-1-carboxylic acid tert-butyl ester (230.00 mg) in methanol (10 mL) was added palladium on carbon 10% (10:90, palladium:carbon black, 40 mg). The mixture was shaken in a Parr apparatus under an atmosphere of hydrogen (35 PSI) for 2 h. Filtration through Celite and evaporation of the solvent provided (±)-4-(4-amino-3-methoxy-phenyl)-3,3-difluoro-piperidine-1-carboxylic acid tert-butyl ester (200 mg, 95% yield), which was used without purification. $^1$H NMR ($CDCl_3$): δ ppm 6.65-6.77 (m, 3H), 4.15-4.65 (m, 2H), 3.85 (s, 3H), 3.77 (br. s., 2H), 2.72-3.13 (m, 3H), 2.03-2.24 (m, 1H), 1.85 (d, J=12.4 Hz, 1H), 1.49 (s, 9H) 3124-67

12h). 7-(2-Methoxy-pyridin-3-yl)-pyrrolo[2,1-f][1,2,4]triazin-2-ol (prepared as described in U.S. Pat. No. 8,471,005/Appl. WO2010071885; 65 mg, 0.27 mmol) and (±)-4-(4-amino-3-methoxy-phenyl)-3,3-difluoro-piperidine-1-carboxylic acid tert-butyl ester (100 mg, 0.29 mmol) were converted to the title compound by a procedure similar to Example 4, to afford a yellow foam (86 mg, 69% yield). $^1$H NMR ($CDCl_3$): 8.72 (s, 1H), 8.49 (d, J=7.4 Hz, 1H), 8.28 (d, J=8.2 Hz, 1H), 8.24 (m, 1H), 7.51 (s, 1H), 7.14 (d, J=4.0 Hz, 1H), 7.08 (m, 1H), 6.86 (m, 3H), 4.02 (s, 3H), 3.92 (s, 3H), 3.30 (m, 1H), 3.21 (m, 1H), 3.02 (m, 1H), 2.90 (dd, J=30.8 (F_H vic. coupling), 13.7 Hz, 1H), 2.75 (m, 1H), 2.10 (m, 1H), 1.95 (m, 2H); LC/MS (ESI+): 467.0 (M+H).

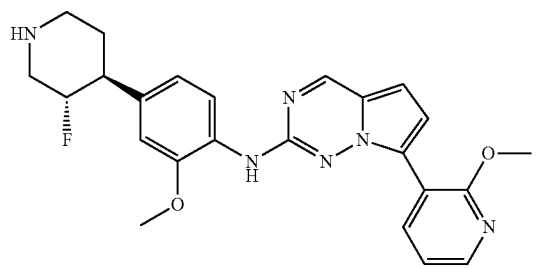 [SMILES: COc1cc([C@@H]2CCNC[C@H]2F)ccc1Nc1ncc2ccc(-c3cccnc3OC)n2n1]

Example 13

(±)-[4-(3,4-trans-3-Fluoro-piperidin-4-yl)-2-methoxy-phenyl]-[7-(2-methoxy-pyridin-3-yl)-pyrrolo[2,1-f][1,2,4]triazin-2-yl]-amine 7-(2-methoxy-pyridin-3-yl)-pyrrolo[2,1-f][1,2,4]triazin-2-ol (prepared as described in U.S. Pat. No. 8,471,005/Appl. WO2010071885; 100 mg, 0.41 mmol) and (±)-4-(4-amino-3-methoxy-phenyl)-3-fluoro-piperidine-1-carboxylic acid tert-butyl ester (Intermediate 5b, Scheme 2; 146 mg, 0.45 mmol) were converted to the title compound by a procedure similar to Example 4, to afford a yellow foam (119 mg, 64% yield). ¹H NMR (CDCl₃): δ ppm 8.70 (s, 1H), 8.49 (d, J=7.6 Hz, 1H), 8.28 (d, J=8.1 Hz, 1H), 8.19-8.26 (m, 1H), 7.48 (s, 1H), 7.13 (d, J=4.3 Hz, 1H), 7.01-7.09 (m, 1H), 6.77-6.87 (m, 3H), 4.46-4.69 (m, 1H), 4.02 (s, 3H), 3.91 (s, 3H), 3.44-3.50 (m, 2H), 3.08 (d, J=11.9 Hz, 1H), 2.60-2.80 (m, 3H), 1.68-1.83 (m, 2H).

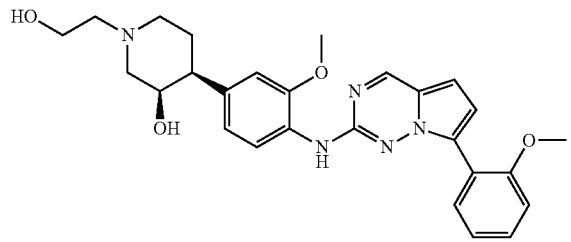 [SMILES: COc1cc([C@@H]2CCN(CCO)C[C@@H]2O)ccc1Nc1ncc2ccc(-c3ccccc3OC)n2n1]

Example 14

(±)-3,4-cis-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol Racemic Example 14, (±)-3,4-cis-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol, was prepared as described in U.S. Pat. No. 8,471,005/Appl. WO2010071885 and in Scheme 1.

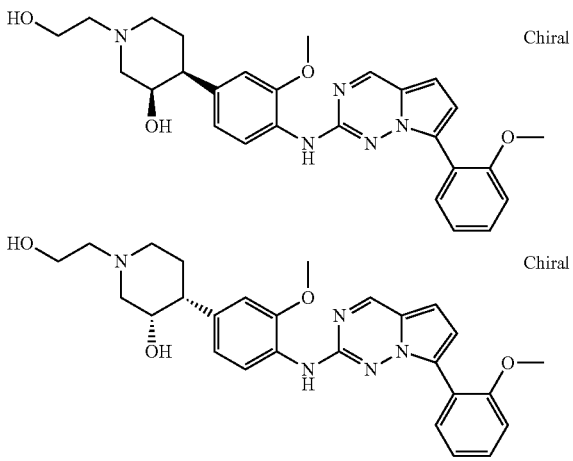

Examples 14a and 14b (3R,4S)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol and (3S,4R)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol Enantiomerically pure Examples 14a and 14b were prepared by chromatographic separation from the racemic Example 14 (exemplified in U.S. Pat. No. 8,471,005/Appl. WO2010071885) by a SFC procedure similar to the one described for Examples 16a and 16b. Example 14a (ee>99%) is first to elute from the column, and Example 14b is the second to elute from the column (ee>99%).

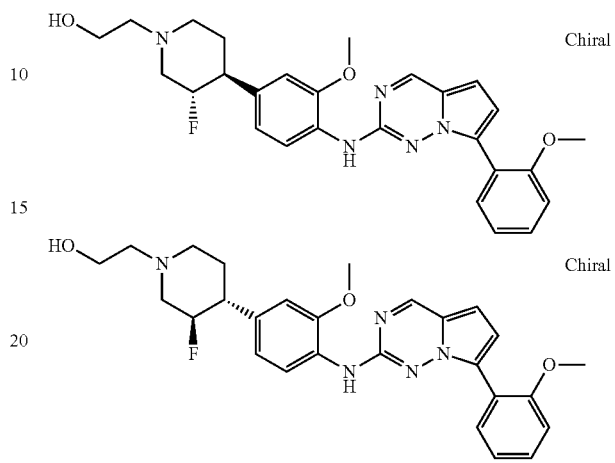

Examples 15a and 15b 2-((3S,4S)-3-Fluoro-4-{3-methoxy-4-[7-(2-methoxy-phenyl)-pyrrolo[2,1-f][1,2,4]triazin-2-ylamino]-phenyl}-piperidin-1-yl)-ethanol and 2-((3R,4R)-3-Fluoro-4-{3-methoxy-4-[7-(2-methoxy-phenyl)-pyrrolo[2,1-f][1,2,4]triazin-2-ylamino]-phenyl}-piperidin-1-yl)-ethanol Enantiomerically pure Examples 15a and 15b were prepared by chromatographic separation from the racemic Example 3 by a SFC procedure similar to the one described for Examples 16a and 16b. Example 15a (ee>99%) is first to elute from the column, and Example 15b is the second to elute from the column (ee>99%).

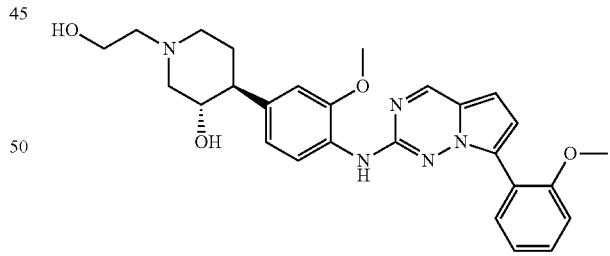

Example 16

(±)-3,4-trans-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol 16a) The reaction was placed under an atmosphere of nitrogen. To a cold 0° C. solution of 4-(3-methoxy-4-nitro-phenyl)-3,6-dihydro-2H-pyridine-1-carboxylic acid tert-butyl ester (intermediate 4, 4.0 g, 12.0 mmol) in dry dimethoxyethane (10 ml) was added sodium borohydride (728 mg, 19.2 mmol) in one portion. After 5 minutes a solution of boron trifluoride etherate (3.0 mL, 24 mmol) in dry dimethoxyethane (5 mL) was added dropwise (syringe), and then the cooling bath removed and the reaction was stirred overnight (while warming to room temperature). The reaction was cooled to 0° C. and water was added dropwise until effervescence ceased (quench of excess hydride species), followed by a 10 M solution of sodium hydroxide in water (7.6 mL, 76 mmol) and then 30% aq. hydrogen peroxide (7.6 mL, 74 mmol) dropwise. After the addition, the reaction was allowed to warm to room temperature and stirred for 2 h. Diluted with water and then extracted with EtOAc. The combined extracts were washed with 3% aq. NH$_3$, then water, dried (MgSO4), filtered, evaporated, and the residue purified by flash chromatography (ISCO, Silicagel, EtOAc/Hexanes 25-40%) to give 2 g (47% yield) of intermediate 16a, (±)-3,4-trans-3-hydroxy-4-(3-methoxy-4-nitro-phenyl)-piperidine-1-carboxylic acid tert-butylester.

16b). To a solution of (±)-3,4-trans-3-hydroxy-4-(3-methoxy-4-nitro-phenyl)-piperidine-1-carboxylic acid tert-butylester (intermediate 16a, 7 g) in methanol (350 mL) was added palladium on carbon 10% (10:90, Palladium:carbon black, 1 g). The mixture was shaken in a Parr apparatus under an atmosphere of hydrogen (35 PSI) overnight. Filtration through Celite and evaporation of the solvent provided the crude product. The crude product was worked-up by suspension in dichlormethane and washing twice with diluted aq. NaHCO$_3$, drying on Na$_2$SO$_4$, filtration and evaporation of solvent. The product was purified by flash chromatography (Silicagel, EtOAc/hexanes ~40-70%) to give 5.1 g (80% yield) of intermediate 16b, (±)-3,4-trans-4-(4-amino-3-methoxy-phenyl)-3-hydroxy-piperidine-1-carboxylicacid tert-butyl ester.

Intermediate 16b was converted to racemic Example 16 as outlined in Scheme 4 and described in detail in U.S. Pat. No. 8,471,005 (Appl. WO2010071885).

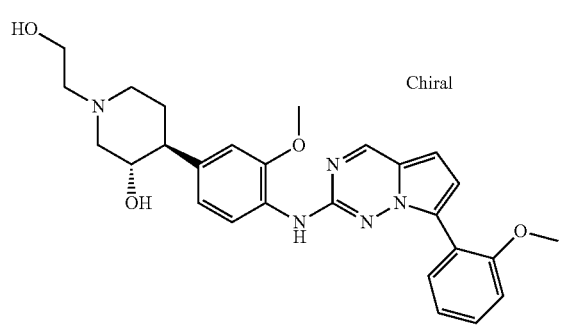

16a

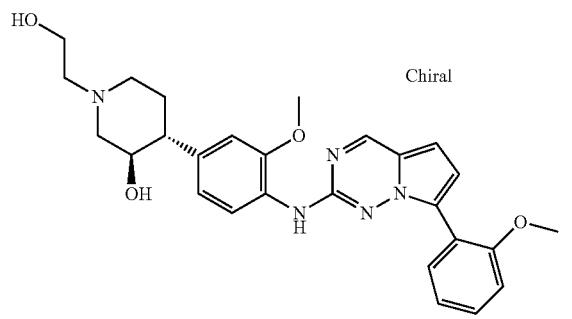

16b

Example 16a (3S,4S)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol and

Example 16b (3R,4R)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol Separation of Enantiomers:

Examples 16a and 16b were obtained from Example 16 as follows: Racemic Example 16 (exemplified in U.S. Pat. No. 8,471,005/Appl. WO2010071885) was subjected to enantiomeric separation by supercritical fluid (SFC) high performance liquid chromatography on chiral stationary phase column to generate isolated single enantiomer Examples 16a and 16b. A ChiralPak AD-H (10×150 mm or 21×150 mm) was used, at a temperature T=35° C. and back pressure P=120 bar, with a UV detector set at 220 nm wavelength. The flow rate was 6.0 mL/min and the mobile phase was 40% MeOH (with 0.1% DEA)—60% CO$_2$. Example 16a (ee>99%) is first to elute from the column, and Example 16b is the second to elute from the column (ee>99%).

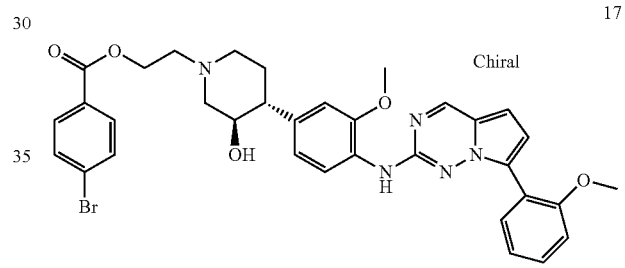

17

Example 17

4-Bromo-benzoic acid 2-((3R,4R)-3-hydroxy-4-{3-methoxy-4-[7-(2-methoxy-phenyl)-pyrrolo[2,1-f][1,2,4]triazin-2-ylamino]-phenyl}-piperidin-1-yl)-ethyl ester To a mixture of (3R,4R)-1-(2-hydroxy-ethyl)-4-{3-methoxy-4-[7-(2-methoxy-phenyl)-pyrrolo[2,1-f][1,2,4]triazin-2-ylamino]-phenyl}-piperidin-3-ol (Example 16b; 40.00 mg, 0.082 mmol) and triethylamine (12 uL, 0.09 mmol) in methylene chloride (0.400 mL, 6.24 mmol) was added 4-bromo-benzoyl chloride, (19 mg, 0.086 mmol) at 0° C. The reaction was stirred overnight allowing the cooling bath/reaction to slowly warm to room temperature. The volatile were evaporated and the crude residue was further dried on high vacuum, The product was isolated by preparative reverse phase hplc (Gilson) and the free base was released by using a strong cation exchange resin column (Strata, from Phenomenex) to give 33 mg (60% yield) of 4-bromo-benzoic acid 2-((3R,4R)-3-hydroxy-4-{3-methoxy-4-[7-(2-methoxy-phenyl)-pyrrolo[2,1-f][1,2,4]triazin-2-ylamino]-phenyl}-piperidin-1-yl)-ethyl ester. $^1$H NMR (CDCl$_3$): 8.70 (br s, 1H), 8.35 (d, J=8.1 Hz, 1H), 7.96 (d, J=7.6 Hz, 1H), 7.92 (d, J=8.4 Hz, 2H), 7.60 (d, J=8.4 Hz, 2H), 7.47 (br s, 1H), 7.46-7.40 (m, 1H), 7.12 (app t, J=7.5

Hz, 1H), 7.07 (d, J=8.3 Hz, 1H), 7.02 (d, J=4.7 Hz, 1H), 6.85 (d, J=4.7 Hz, 1H), 6.78 (d, J=8.7 Hz, 1H), 6.76 (br s, 1H), 4.50 (app t, J=5.8 Hz, 2H), 3.89 (s, 3H), 3.84 (s, 3H), 3.80 (m, 1H), 3.31 (m, 1H), 3.04 (br d, J=11.3 Hz, 1H), 2.90 (app t, J=5.8 Hz, 2H), 2.35 (m, 1H), 2.26 (m, 1H), 2.15 (app t, J=10.2 Hz, 1H), 1.86 (m, 2H), 1.67 (br s, 1H).

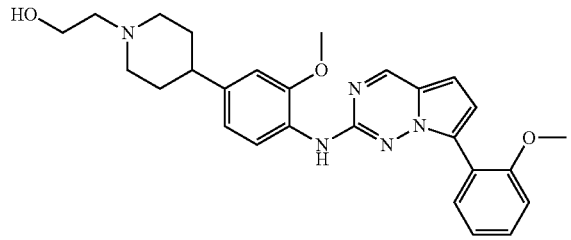 [SMILES: COc1cc(C2CCN(CCO)CC2)ccc1Nc1ncc2ccc(-c3ccccc3OC)n2n1]

Example 18

2-(4-{3-Methoxy-4-[7-(2-methoxy-phenyl)-pyrrolo[2,1-f][1,2,4]triazin-2-ylamino]-phenyl}-piperidin-1-yl)-ethanol

[7-(2-Methoxy-phenyl)-pyrrolo[2,1-f][1,2,4]triazin-2-yl]-(2-methoxy-4-piperidin-4-yl-phenyl)-amine (60 mg, 0.14 mmol) was prepared in 60% yield from 7-(2-methoxy-phenyl)-pyrrolo[2,1-f][1,2,4]triazin-2-ol (described in U.S. Pat. No. 8,471,005/Appl. WO2010071885) and 4-(4-amino-3-methoxy-phenyl)-piperidine-1-carboxylic acid tert-butyl ester in manner similar to Example 4, and converted to the title compound by a procedure similar to the one described for Example 8 to give a yellow foam (35 mg, 53% yield). $^1$H NMR (CDCl$_3$): 8.69 (s, 1H), 8.29 (d, J=7.7 Hz, 1H), 8.99 (d, J=7.6 Hz, 1H), 7.43 (m, 2H), 7.13 (m, 1H), 7.07 (d, J=8.3 Hz, 1H), 7.02 (d, J=2.7 Hz, 1H), 6.83 (d, J=2.7 Hz, 1H), 6.73 (s, 1H), 6.72 (m, 1H), 3.90 (s, 3H), 3.84 (s, 3H), 3.65 (m, 2H), 3.05 (m, 2H), 2.59 (m, 2H), 2.48 (m, 1H), 2.19 (m, 2H), 1.79 (m, 5H); LC/MS (ESI+): 474.0 (M+H).

Assignment of Absolute Stereochemistry for Example 16b

X-Ray Data for Example 17

Figure 3:
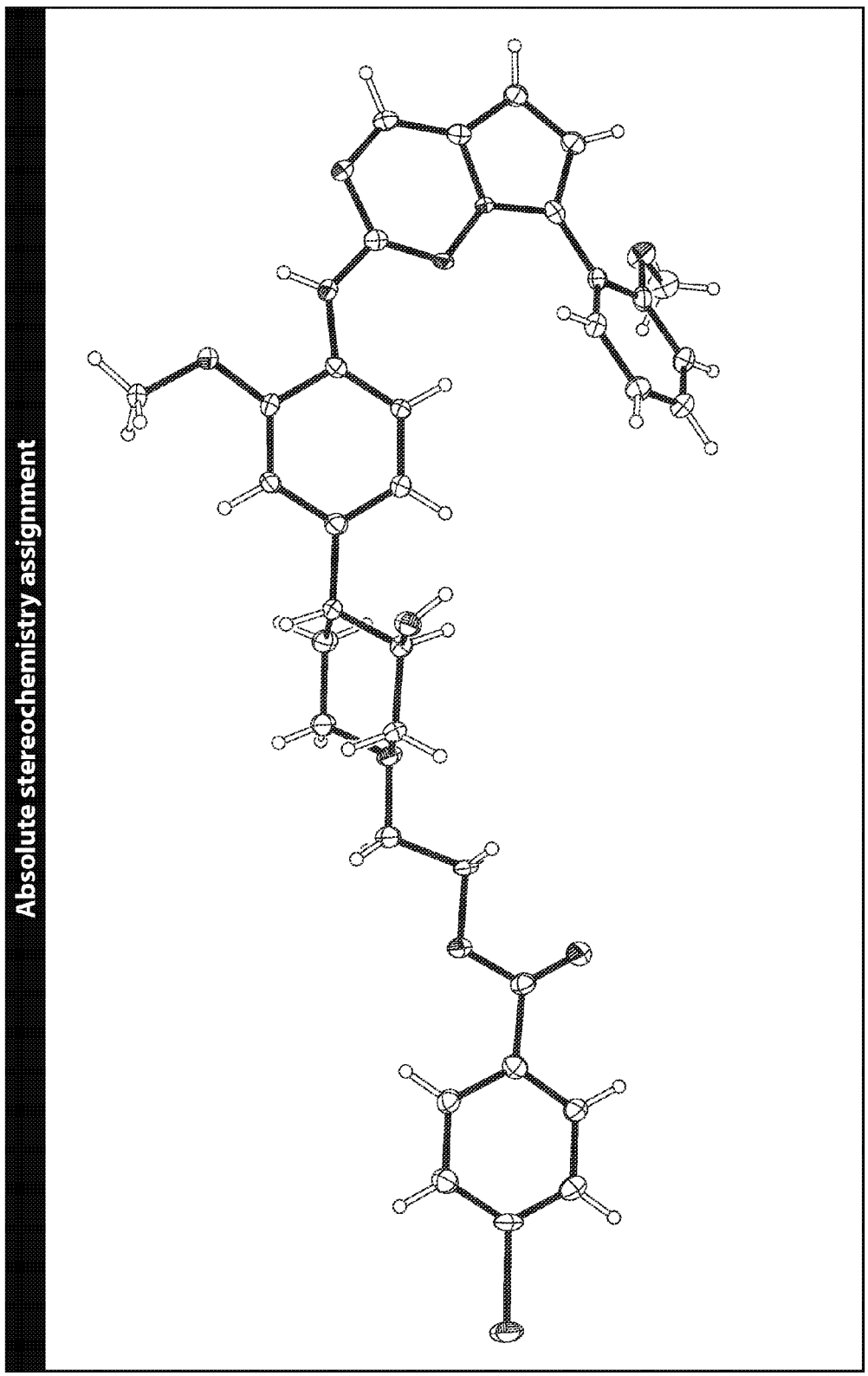
FIG. 3 depicts the absolute stereochemical assignment of compound 17 via heavy-atom anomalous dispersion x-ray crystallography.

Enantiomerically pure Example 16b was derivatized to Example 17 as shown in Scheme 5 and in the previous section. The absolute stereochemistry was established by x-ray crystallography, as described below. Based on the heavy-atom effect (cf. also Mudianta, I. W. Katavic, P. L.; Lambert, L. K. et al. *Tetrahedron* 2010, 66, 2752 for other examples) of the bromine atom, the absolute stereochemistry of Examples 17 and 16b was assigned via anomalous dispersion x-ray crystallography to be (3R,4R). The ORTEP diagram is shown in FIG. 3.

X-Ray Crystallography Experimental Procedure

Example 17

All reflection intensities were measured using a KM4/Xcalibur (detector: Sapphire3) with enhance graphite-monochromated Mo Kα radiation (λ=0.71073 Å) under the program CrysAlisPro (Version 1.171.33.55, Oxford Diffraction Ltd., 2010). The program CrysAlisPro (Version 1.171.33.55, Oxford Diffraction Ltd., 2010) was used to refine the cell dimensions. Data reduction was done using the program CrysAlisPro (Version 1.171.33.55, Oxford Diffraction Ltd., 2010). The structure was solved with the program SHELXS-97 (Sheldrick, 2008) and was refined on F$^2$ with SHELXL-97 (Sheldrick, 2008). Analytical numeric absorption corrections based on a multifaceted crystal model were applied using CrysAlisPro (Version 1.171.33.55, Oxford Diffraction Ltd., 2010). The temperature of the data collection was controlled using the system Cryojet (manufactured by Oxford Instruments). The H-atoms (except for the H atoms located on N2n and O3n, n=A, B) were placed at calculated positions using the instructions AFIX 13, AFIX 23, AFIX 43 or AFIX 137 with isotropic displacement parameters having values 1.2 or 1.5 times Ueq of the attached C atoms. The H-atoms located on N2n and O3n (n=A, B) were found from difference Fourier maps, and their positions were restrained so that the N—H and O—H distances refine to 0.88(3) and 0.84(3) Å, respectively.

Data were collected at 110(2) K after the crystal has been flash-cooled. The structure of the compound $C_{34}H_{34}BrN_5O_5$ was solved and refined in the non-centrosymmetric space group P1 with Z'=2 (i.e., there are two crystallographically independent molecules in the asymmetric unit). The structure of Example 17 is ordered. The absolute configuration was established by anomalous-dispersion effects in diffraction measurements on the crystal, and the model has chirality R on C11n and C12n (n=A, B). The two chiral centers are found in the trans conformation. The Flack parameter refines to −0.019(5) (note: a value of 0 for this parameter indicated that the absolute structure given by the structure refinement has been correctly assigned).

The final refinement against F$^2$ was acceptable. The R factor [F$^2$>2σ(F$^2$)] is about 0.044. The final difference Fourier map was relatively flat, and the residual peaks are no larger than 0.67 e Å$^{-3}$. The residual peaks Q1 (0.67 e Å$^{-3}$) and Q3 (0.43 e Å$^{-3}$) seems to be found at sites, which might be potential acceptors in N—H'''A (A=acceptor). However, these peaks are too small to be lattice water molecules. $C_{34}H_{34}BrN_5O_5$, Fw=672.57, yellow rod, 0.40×0.15×0.10 mm$^3$, triclinic, P1 (no. 1), a=7.32713(12), b=11.12781(17), c=19.6664(3) A, α=106.2111(14), β=91.7015(13), γ=93.2437(12°), V=1535.54(4) Å$^3$, Z=2, D$_x$=1.455 g cm$^{-3}$, μ=1.390 mm$^{-1}$, abs. corr. range: 0.631-0.905. 37796 Reflections were measured up to a resolution of (sin θ/λ)$_{max}$=0.62 Å$^{-1}$. 12019 Reflections were unique (R$_{int}$=0.0380), of which 10778 were observed [I>2σ(I)]. 827 Parameters were refined with 7 restraints. R1/wR2 [I>2σ(I)]: 0.0442/0.1187. R1/wR2 [all refl.]: 0.0486/0.1202. S=1.092. Residual electron density found between −0.47 and 0.68 e Å$^{-3}$.

Biological Data

Experimental procedures for determination of inhibitory activity (IC$_{50}$) against ALK autophosphorylation in enzyme assay and cellular assay were performed as described in U.S. Pat. No. 8,471,005 and in Cheng M., Quail M. R., Gingrich D. E., et al. *Mol Cancer Ther* 2012; 11, 670-679. The inhibitory activities for the exemplified compounds are given in Table 1.

TABLE 1

ALK Inhibitory activity for Examples 1-18.

| Example | ALK IC50 (nM) | ALK Cell IC50 (nM) |
|---|---|---|
| 1 | 3.33 | 50 |
| 2 | 8.23 | 80 |
| 3 | 9.51 | 60 |
| 4 | 13.98 | 250 |
| 5 | 5.66 | 250 |
| 6 | 11.13 | 120 |
| 7 | 9.48 | 130 |
| 8 | 12.76 | |
| 9 | 28.16 | |
| 10 | 25.19 | |
| 11 | 34.03 | |
| 12 | 13.74 | 200 |
| 13 | 9.81 | 250 |
| 14 | 3.00 | 60 |
| 14a | 4.12 | 40 |
| 14b | 2.23 | 40 |
| 15a | 6.53 | 60 |
| 15b | 9.61 | 200 |
| 16 | 5.00 | 50 |
| 16a | 3.76 | 100 |
| 16b | 3.52 | 120 |
| 17 | | |
| 18 | 3.00 | 150 |

Rat Pharmacokinetic (PK) Studies.

Experimental protocols for rat PK determinations followed procedures previously described (Ott, G. R.; Wells, G. J.; Thieu, T. V.; Quail, M. R. et al. *J. Med. Chem.* 2011, 54, 6328-6341). Examples 14 (racemic, cis) and 16 (racemic, trans) were identified as having acceptable rat PK properties. See Table 2 below.

TABLE 2

Sprague-Dawley Rat Pharmacokinetic Parameters.

| | PK prameters | 14 | 16 |
|---|---|---|---|
| i.v. | dose (mg/kg) | 1 | 1 |
| | $t_{1/2}$ (h) | 2.5 ± 0.6 | 3.2 ± 0.6 |
| | $AUC_{0-\infty}$ (ng * h/mL) | 371 ± 6 | 459 ± 72 |
| | Vd (L/kg) | 9.9 ± 2 | 10.3 ± 1.3 |
| | CL (mL/min/kg) | 46 ± 1 | 39 ± 7 |
| p.o. | dose (mg/kg) | 5 | 5 |
| | $C_{max}$ (ng/mL) | 85 ± 15 | 97 ± 10 |
| | $t_{max}$ (h) | 6 ± 0 | 4 ± 1.2 |
| | $AUC_{0-\infty}$ (ng * h/mL) | 479 ± 83 | 708 ± 63 |
| | F % | 26 ± 4 | 31 ± 3 |

The rat PK parameters for the two diastereomeric racemates Example 14 and Example 16 were comparable.

In Vivo Studies

General Experimental Procedures:

In vivo PK/PD and tumor growth inhibition studies in rodents were performed according to the protocols described below, previously published in: Cheng M., Quail M. R., Gingrich D. E., et al. *Mol Cancer Ther* 2012; 11, 670-679 and Ott, G. R.; Wells, G. J.; Thieu, T. V.; Quail, M. R. et al. *J. Med. Chem.* 2011, 54, 6328-6341.

Cell Lines

The NPM-ALK-positive ALCL cell lines, Karpas-299 and Sup-M2, were purchased from Deutsche Sammlung von Mikroorganismen und Zellkulturen GmbH.

Animals

Severe combined immunodeficient (SCID)/beige or nu/nu mice (6- to 8-week-old female) were maintained 5 per cage in microisolator units on a standard laboratory diet (Teklad Labchow). Animals were housed under humidity- and temperature-controlled conditions and the light/dark cycle was set at 12-hour intervals, maintained under specified and opportunistic pathogen-free conditions. Mice were quarantined at least 1 week before experimental manipulation. All animal studies were conducted under protocol approved by the Institutional Animal Care and Use Committee of Cephalon, Inc. or by University of Turin Ethical Committee.

Immunoblot Analysis

Immunoblotting of phospho- and total ALK as well as the downstream targets was carried out according to the protocols provided by the antibody suppliers. In brief, after treatment, cells were lysed in FRAK lysis buffer [10 mmol/L Tris, pH 7.5, 1% Triton X-100, 50 mmol/L sodium chloride, 20 mmol/L sodium fluoride, 2 mmol/L sodium pyrophosphate, 0.1% BSA, plus freshly prepared 1 mmol/L activated sodium vanadate, 1 mmol/L DTT, and 1 mmol/L phenylmethylsulfonylfluoride, protease inhibitors cocktail III (1:100 dilution, catalog no. 539134; Calbiochem)]. After brief sonication, the lysates were cleared by centrifugation, mixed with sample buffer, and subjected to SDS-PAGE. Following transfer to membranes, the membranes were blotted with individual primary and secondary antibodies, washed in TBS/0.2% Tween, and protein bands visualized with Enhanced Chemiluminescence. The individual bands of phospho- and total NPM-ALK were scanned and quantified with the Gel-Pro Analyzer software (Media Cybernetics, Inc.).

PK/PD Studies

Exponentially growing cells were implanted subcutaneously to the left flank of each mouse. The mice were monitored and when the tumor xenograft volumes reached approximately 300 to 500 mm3, mice received a single oral administration of either vehicle PEG-400 or the compound of interest (e.g., Examples 14, 16, 16a, and/or 16b) formulated in vehicle. At indicated time points postdosing, the mice were sacrificed, the blood was collected and centrifuged, and the plasma was collected. The tumors were excised and disrupted with a hand-held tissue blender in completed FRAK lysis buffer without Triton X-100. After brief sonication, the lysates were cleared by centrifugation, mixed with sample buffer, and subjected to SDS-PAGE for ALK immunoblotting as described above. The individual bands of phospho- and total NPM-ALK were scanned and quantified with the Gel Pro Analyzer software (Media Cybernetics, Inc.). The relative NPM-ALK tyrosine phosphorylation (phospho-NPMALK/NPM-ALK ratio) of each sample at indicated time points was then calculated, with the average value of vehicle-treated sample(s) as 100. The compound levels in plasma and tumor lysates were measured by liquid chromatography/tandem mass spectrometry (LC/MS-MS).

PK/PD Results and Discussion

Racemic Examples 14 (cis relative stereochemistry) and 16 (trans relative stereochemistry) showed favorable and comparable in vitro profiles and rat PK properties (Table 2). Therefore, to evaluate their ability to inhibit the autophosphorylation of NPM-ALK in vivo, both racemic compounds were advanced into single dose PK/PD experiments in subcutaneous ALK-dependent Sup-M2 xenografts in Scid mice (FIGS. 1A and 1B, respectively). In these experiments, racemic Example 14 exhibited modest inhibition of ALK phosphorylation when dosed orally at 30 mg/kg, with <75% inhibition relative to the vehicle-only treated animals, at any time point up to 24 h (FIG. 1A). The separated, single enantiomers of Example 14, Examples 14a and 14b both showed comparably modest inhibition when dosed at 30 mg/kg in independent PK/PD experiments (data not shown).

To contrast, racemic Example 16 (trans) effected 75-87% inhibition of ALK phosphorylation up to 12 h after an equivalent dose, albeit followed by recovery of the signal at the 24 h time point (FIG. 1B). This positive result was unpredictable in view of the comparable in vitro data between Examples 14 and 16. Furthermore, the separated single enantiomers Example 16a and Example 16b gave different in vivo PK/PD responses when tested independently, which is an unpredicted result based on their comparable in vitro activity profiles. Specifically, Example 16a has an enzyme IC50 of 3.76 nM and a cell IC50 of 100 nM, whereas Example 16b has an enzyme IC50 of 3.52 nM and a cell IC50 of 120 nM. (See Table 1) Despite the comparable in vitro data, single enantiomer Example 16a had only a modest impact on the ALK autophosphorylation: 40-60% inhibition over 16 h post single p.o. dose of 30 mg/kg (FIG. 1C), whereas single enantiomer Example 16b inhibited 80-100% of the signal up to 16 h, under the same experimental conditions (FIG. 1D). Plasma and tumor levels achieved with Example 16b (FIG. 1F) at 6 h and 16 h post dose were also unexpectedly higher (in the 4-10 fold range) than the plasma and tumor levels achieved with Example 16a at the same time-points (FIG. 1E). In view of the discovery of these stereoselective in vivo PK/PD responses, the preferred single enantiomer Example 16b was advanced in antitumor efficacy studies, which are described below.

Antitumor Efficacy Studies

Tumor-bearing mice were randomized into different treatment groups (8-10 mice per group) and administered orally either vehicle (PEG-400, or dH2O) or Example 16b formulated in vehicle at indicated doses (expressed as mg/kg equivalents of free base) and with indicated dosing frequency, with 100 mL per dosing volume. The length (L) and width (W) of each tumor was measured with a Vernier caliper and the mouse body weight was determined every 2 to 3 days. The tumor volumes were then calculated with the formula of 0.5236*L*W*(L+W)/2. Statistical analyses of tumor volumes and mouse body weight were carried out using the Mann-Whitney rank sum test. Plasma and tumor samples were obtained at 2 hours post-final dose, and the compound levels in plasma and tumor lysates were measured by LC/MS-MS.

Figure 2:
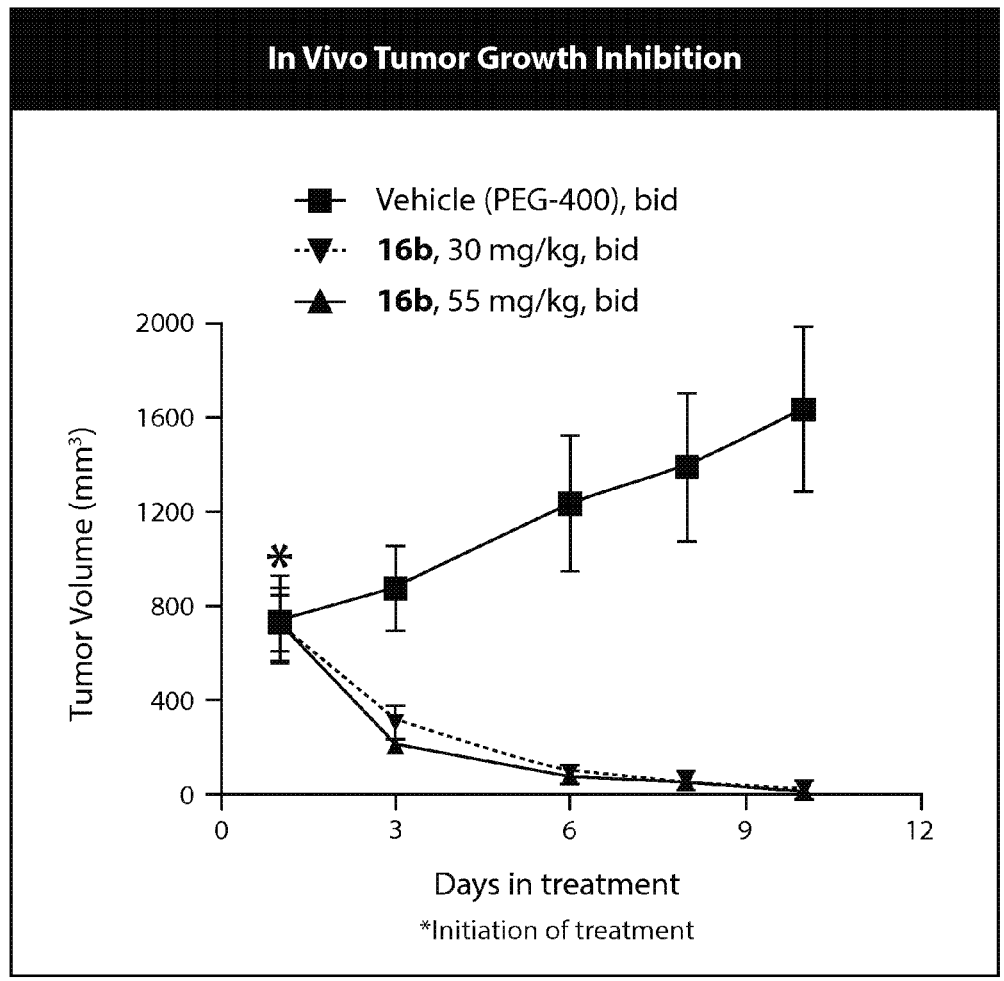
FIG. 2 depicts the anti-tumor efficacy of compound 16b (dosed orally, b.i.d.) in SCID mice bearing Sup-M2 ALCL xenografts.

Based upon the robust PK/PD response, (FIG. 1D), the single enantiomer Example 16b was selected for anti-tumor efficacy studies in Sup-M2 xenografts in Scid mice. Complete tumor regressions were observed upon treatment with either 30 mg/kg or 55 mg/kg of Example 16b b.i.d., p.o. doses for 10 days (FIG. 2). No remaining tumor could be observed after 10 days of dosing. Both dosing regimens were well tolerated, with no body weight loss or other overt toxicity being detected. Such positive results in the in vivo PK/PD and Antitumor Efficacy studies with the single enantiomer Example 16b were not predictable in view of the in vitro or in vivo data for Example 14, Example 16 or Example 16a.

The invention claimed is:
1. A compound of the general formula (I)

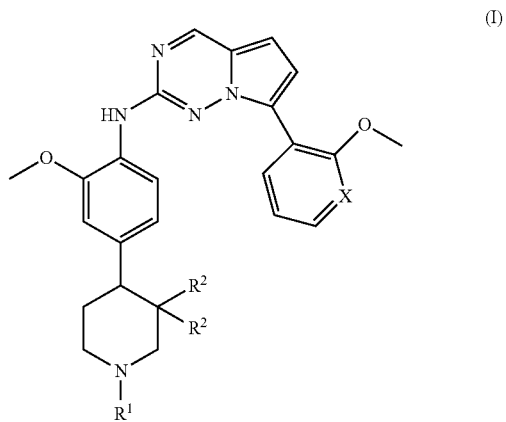

(I)

and/or a salt thereof, wherein:
X is CH or N;
$R^1$ is chosen from H or $C_1$-$C_6$alkyl optionally substituted with at least one $R^3$;
at least one $R^2$ is halogen and the other $R^2$ is chosen from hydrogen or halogen;
each $R^3$ is independently chosen from hydroxyl, $C_1$-$C_6$alkyoxy, $CON(R^4)_2$, and $OCOR^4$; and
each $R^4$ is independently chosen from hydrogen, $C_1$-$C_6$alkyl, and phenyl substituted with at least one halogen.

2. A compound according to claim 1 wherein the other $R^2$ is halogen.
3. A compound according to claim 1 wherein the other $R^2$ is hydrogen.
4. A compound according to claim 1 wherein at least one $R^2$ is fluorine.
5. A compound according to claim 2 wherein the other $R^2$ is fluorine.
6. A compound according to claim 1 wherein X is CH.
7. A compound according to claim 1 wherein X is N.
8. A compound according to claim 1 wherein $R^1$ is H.
9. A compound according to claim 1 wherein $R^1$ is $C_1$-$C_6$alkyl optionally substituted with at least one $R^3$.
10. A compound according to claim 9 wherein the at least one $R^3$ is hydroxyl.
11. A compound according to claim 9 wherein the at least one $R^3$ is $C_1$-$C_6$alkyoxy.
12. A compound according to claim 9 wherein the at least one $R^3$ is $CON(R^4)_2$.
13. A compound according to claim 9 wherein the at least one $R^3$ is $OCOR^4$.
14. A compound according to claim 1 wherein $R^4$ is hydrogen.
15. A compound according to claim 1 wherein $R^4$ is $C_1$-$C_6$alkyl.
16. A compound according to claim 1 wherein $R^4$ is phenyl substituted with at least one halogen.
17. A compound according to claim 16 wherein $R^4$ is phenyl substituted with at least one bromine.
18. A pharmaceutical composition comprising a compound according to claim 1, and/or a salt thereof, and a pharmaceutically acceptable excipient.
19. A method of inhibiting ALK kinase in a subject in need thereof, comprising administering to the subject a therapeutically effective amount of a compound according to claim 1, and/or a salt thereof.

20. A method of treating a ALK-positive disease/disorder in a patient in need thereof, comprising administering to the subject a therapeutically effective amount of a compound according to claim 1, and/or a salt thereof.

* * * * *